US008582108B2

(12) United States Patent
Walters

(10) Patent No.: US 8,582,108 B2
(45) Date of Patent: *Nov. 12, 2013

(54) INTEGRATED PLASMONIC SENSING DEVICE AND APPARATUS

(71) Applicant: Integrated Plasmonics Corporation, Palo Alto, CA (US)

(72) Inventor: Robert Joseph Walters, Redwood City, CA (US)

(73) Assignee: Integrated Plasmonics Corporation, San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/717,201

(22) Filed: Dec. 17, 2012

(65) Prior Publication Data
US 2013/0100454 A1 Apr. 25, 2013

Related U.S. Application Data

(63) Continuation of application No. 13/440,808, filed on Apr. 5, 2012, now Pat. No. 8,358,419.

(60) Provisional application No. 61/472,188, filed on Apr. 5, 2011, provisional application No. 61/472,154, filed on Apr. 5, 2011.

(51) Int. Cl.
*G01N 21/55* (2006.01)
(52) U.S. Cl.
USPC ............. 356/445; 438/73; 257/443; 428/64.1
(58) Field of Classification Search
USPC .................... 356/445–448, 301; 257/443, 21; 428/64.1, 64.5, 64.6, 913; 427/162; 385/12, 122, 129
See application file for complete search history.

(56) References Cited

U.S. PATENT DOCUMENTS

| 6,078,705 | A | 6/2000 | Neuschafer et al. |
| 6,410,115 | B1 | 6/2002 | Tsai et al. |
| 6,437,345 | B1 | 8/2002 | Bruno-Raimondi et al. |
| 6,448,064 | B1 | 9/2002 | Vo-Dinh et al. |
| 6,469,785 | B1 | 10/2002 | Duveneck et al. |
| 7,483,140 | B1 | 1/2009 | Cho et al. |
| 7,768,650 | B2 | 8/2010 | Bazylenko |
| 7,773,228 | B1 | 8/2010 | Hollingsworth et al. |
| 7,968,836 | B2* | 6/2011 | Cunningham et al. ...... 250/214.1 |
| 8,358,419 | B2* | 1/2013 | Walters ......................... 356/445 |
| 2007/0052049 | A1 | 3/2007 | Bahl et al. |

(Continued)

OTHER PUBLICATIONS

Narayan et al., "Novel strategies for polymer based light sensors," Thin Solid Films 417:75-77, 2002.

(Continued)

*Primary Examiner* — Hoa Pham
(74) *Attorney, Agent, or Firm* — Seed IP Law Group PLLC

(57) ABSTRACT

An integrated plasmonic sensing device is monolithically integrated and provides marker-free detection (eliminating the need to use fluorescent or absorbing markers) and in-situ monitoring of conditions at each detection region. The integrated plasmonic sensing device includes a plasmonic backplane disposed on a monolithically integrated image sensor. One or more plasmonic scattering regions and one or more plasmonic via regions laterally offset from the plasmonic scattering regions are provided in the plasmonic sensing device. Guided plasmonic modes mediate power transfer through the plasmonic backplane to one or more underlying image sensor pixels.

6 Claims, 31 Drawing Sheets

(56) References Cited

U.S. PATENT DOCUMENTS

| | | | |
|---|---|---|---|
| 2008/0198376 A1 | 8/2008 | Poponin | |
| 2008/0280374 A1 | 11/2008 | Potyrailo et al. | |
| 2009/0273779 A1 | 11/2009 | Baumberg et al. | |
| 2010/0178018 A1* | 7/2010 | Augusto | 385/131 |
| 2010/0320444 A1 | 12/2010 | Dutta | |
| 2011/0037981 A1 | 2/2011 | Zhu et al. | |
| 2011/0079869 A1 | 4/2011 | Mazzillo | |
| 2011/0109902 A1 | 5/2011 | Lin et al. | |

OTHER PUBLICATIONS

Palik (ed.), Handbook of Optical Constants of Solids III, Academic Press, 1998, 9 pages.

Raether, Surface Plasmons on Smooth and Rough Surfaces and on Gratings, Springer Tracts in Modern Physics 111:1-133, 1988.

Sonnichsen et al., "A molecular ruler based on plasmon coupling of single gold and silver nanoparticles," Nature Biotechnology 23(6):741-745, Jun. 2005.

Thrush et al., "Integrated bio-fluorescence sensor," Journal of Chromatography A, 1013:103-110, 2003.

Walters et al., "A silicon-based electrical source of surface plasmon polaritons," Nature Materials 9:21-25, Jan. 2010.

Adams et al., "Microfluidic integration on detector arrays for absorption and fluorescence micro-spectrometers," Sensors and Actuators A 104:25-31, 2003.

Ferry et al., "Light trapping in ultrathin plasmonic solar cells," Optics Express 18(S2), Jun. 21, 2010, 9 pages.

Hacia et al., "Detection of heterozygous mutations in BRCA1 using high density oligonucleotide arrays and two-colour fluorescence analysis," Nature Genetics 14:441-447, Dec. 1996.

Kohane et al., Microarrays for an Integrative Genomics, MIT Press, 2003, pp. 69-88.

Koller et al., "Organic plasmon-emitting diode," Nature Photonics 2:684-687, Nov. 2008.

Lal et al., "Nano-optics from sensing to waveguiding," Nature Photonics 1:641-648, Nov. 2007.

Le et al., "Plasmons in the Metallic Nanoparticle-Film System as a Tunable Impurity Problem," Nano Letters 5 (10):2009-2013, 2005.

Morris et al., "A Versatile Semiconductor Platform for Chemical and Biological Sensing (Poster)," Integrated Plasmonics Corporation, Palo Alto, CA, Nov. 16, 2011.

* cited by examiner

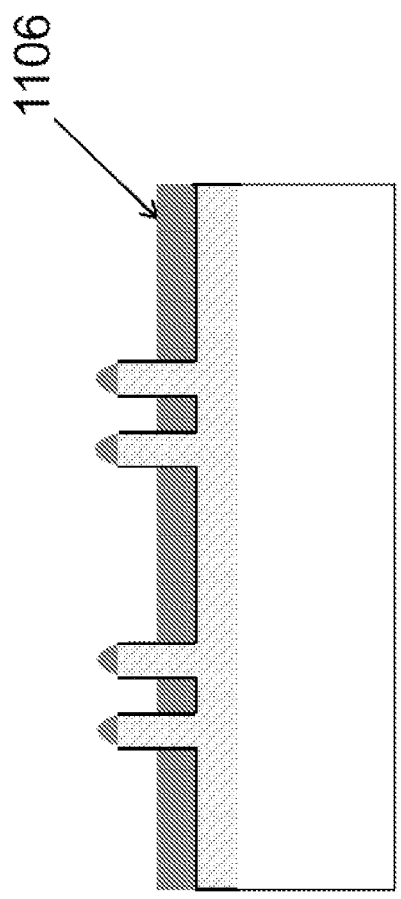
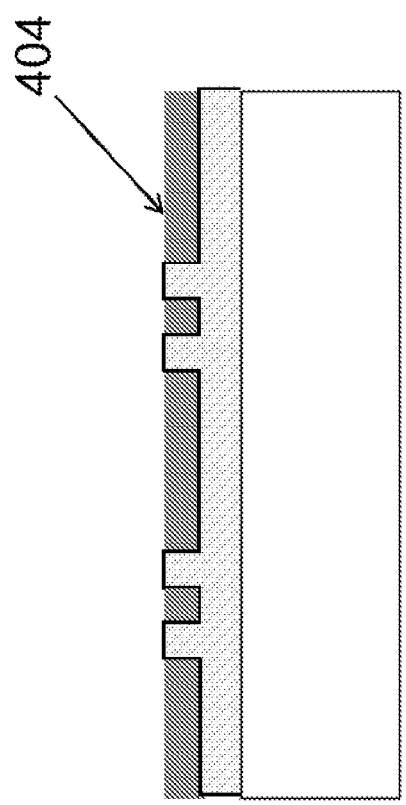
FIG. 11c
FIG. 11d

408

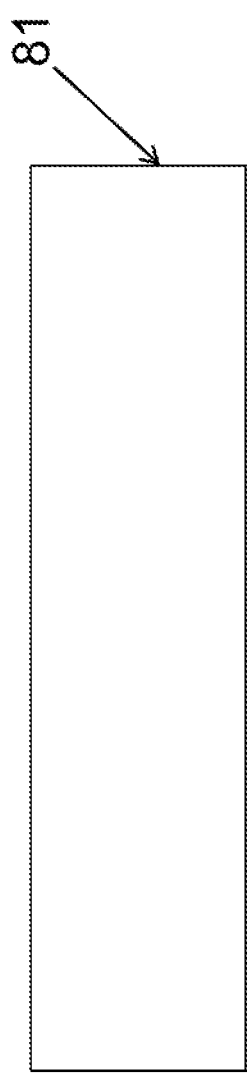
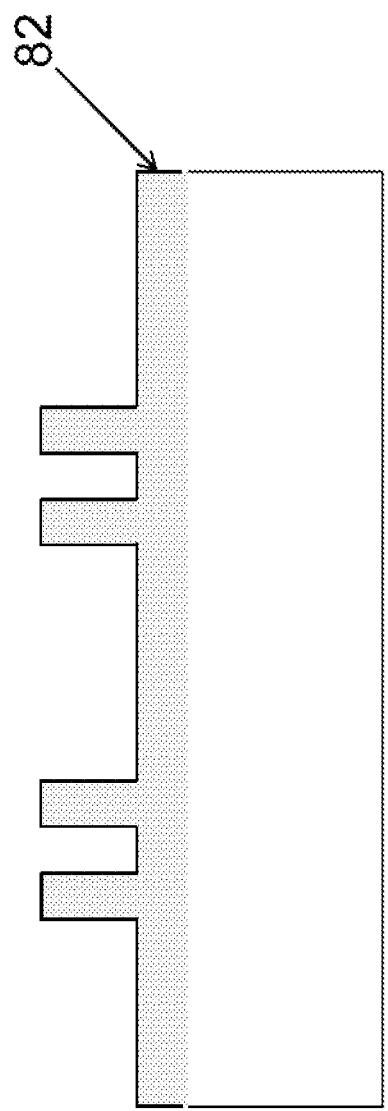
FIG. 20a
FIG. 20b

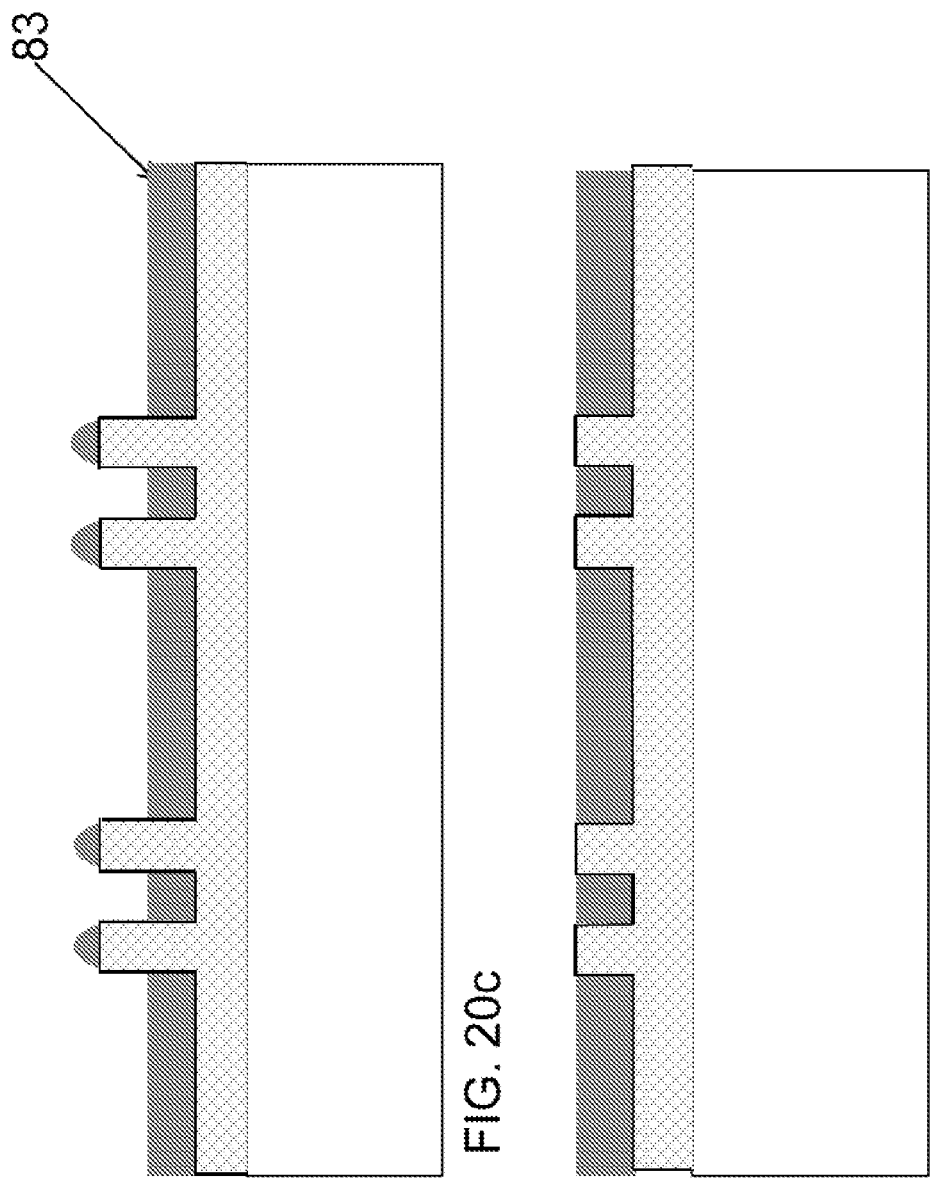

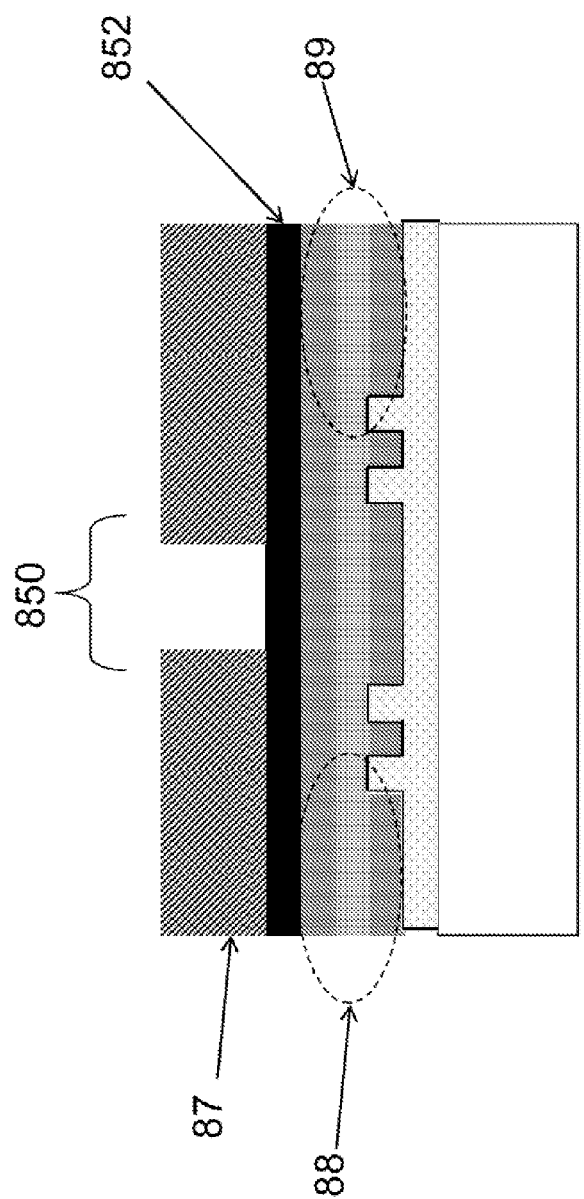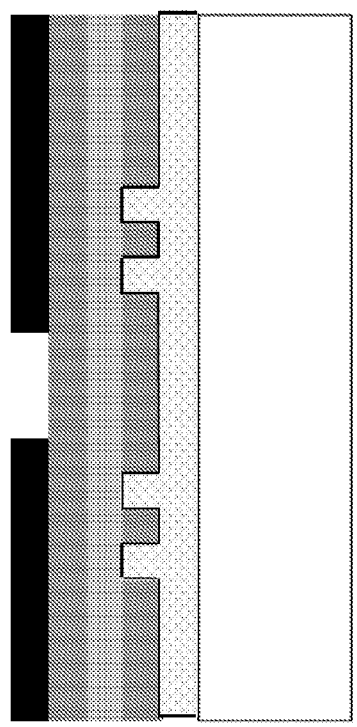
FIG. 20g
FIG. 20h

851

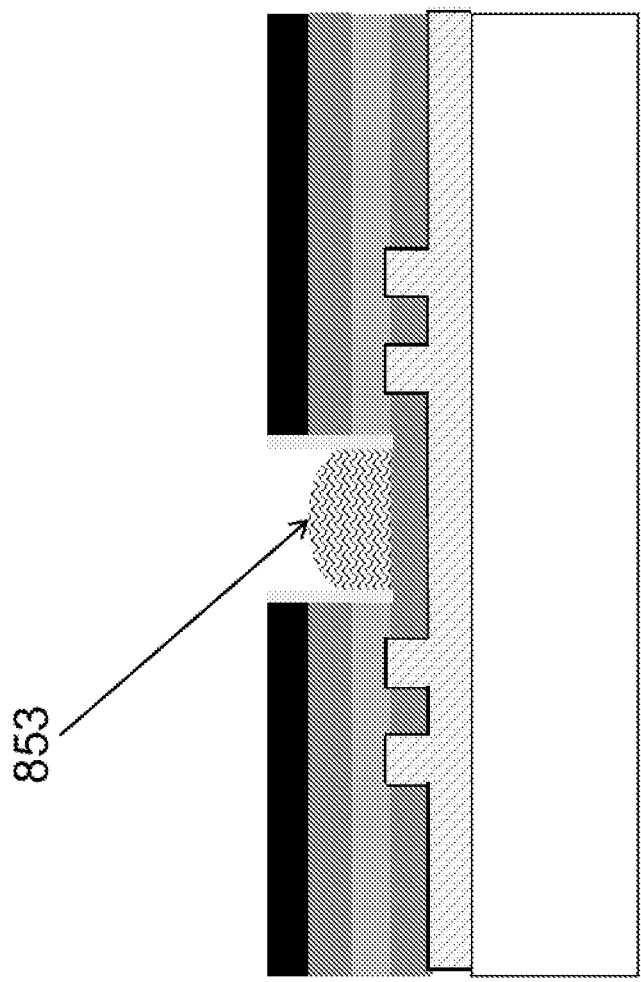

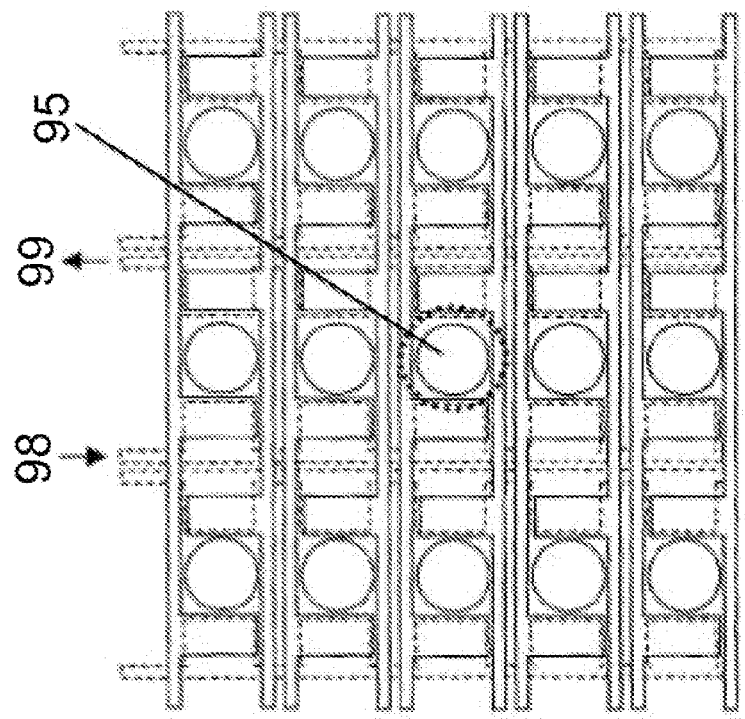
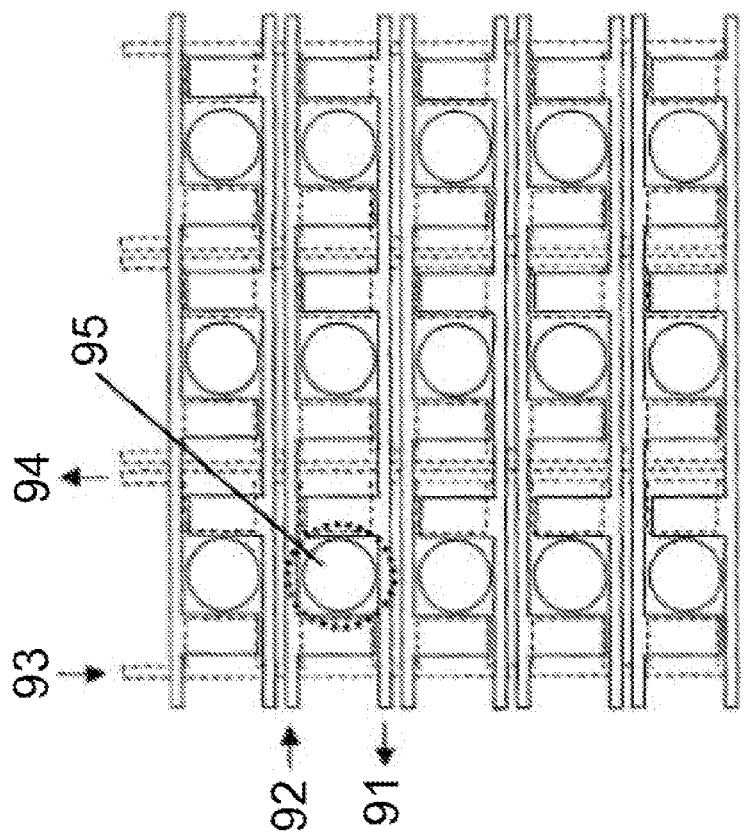
FIG. 21b
FIG. 21a

INTEGRATED PLASMONIC SENSING DEVICE AND APPARATUS

BACKGROUND

1. Technical Field

The present invention relates to the field of plasmonic sensors and optical sensors, in particular to integrated spectroscopic plasmonic sensor devices, integrated plasmonic biosensor devices for oligonucleotide and protein analysis, and integrated plasmonic sensors, in particular, integrated plasmonic micro-array devices for nucleic acid and protein analysis.

2. Description of the Related Art

Spectrometers are devices used to measure properties of light over a portion of the electromagnetic spectrum. The properties of light measured include the intensity of the light and the polarization state of the light. The independent variable is often the wavelength of light or a measure of the photon energy of the light. Spectrometers usually employ a source of electromagnetic energy, various optical devices such as mirrors and gratings as optical interference filters for dispersing the light to the detector, and a detector to detect the light intensity or photon energy as a function of wavelength. Existing devices for detecting the light properties include electronic photodetectors such as charge-coupled devices (CCD), CMOS active pixel sensor arrays, or focal plane arrays. Existing spectrometers find use in many areas, including analyzing compositions of unknown material.

Micro-array technology for expression profiling is well known and is currently widely used in genomic research. Recently much interest has centered on the development of DNA chips based on high density oligonucleotide arrays and fluorescence analysis such as described by Hacia et al. (G. Hacia, L. C. Brody, M. S. Chee. S. P. A. Fodor F. S. Collins in Nature Genetics 14, December 1996). One of the examples of commercialization of this technology has been Affymetrix's "GeneChip", which was developed to process large amounts of genetic information. Affymetrix technology relies on photolithographic processing to produce thousands of detection regions on a single chip. Alternative techniques include robotic spotting and ink-jet printing although they achieve somewhat smaller detection region density within the micro-array.

For the micro-arrays in common use, one typically starts by taking a specific biological substance or system of interest, extracting its mRNA, and making a fluorescence tagged cDNA copy of this mRNA. This tagged cDNA copy, typically called the target, is then hybridized to a slide containing a grid or array of single stranded DNA (ssDNA) called probes which have been built or placed (i.e. immobilized) in specific detection regions on this grid. Similar to the general hybridization principle, a target will only hybridize with its complementary probe i.e., nucleic acid strands tend to be paired to their complements in double-stranded structures. Thus, a single-stranded cDNA target molecule will seek out its complement in a complex mixture of ssDNA containing large numbers of other nucleic acid molecules. Hence, nucleic acid probe (e.g., gene probe) detection methods are very specific to DNA sequences. Factors affecting the hybridization or re-association of two complementary DNA strands include temperature, contact time, salt concentration, the degree of mismatch between the base pair sequences, and the length and concentration of the target and probe sequences. In perhaps the simplest procedure, hybridization is performed on an immobilized probe molecule attached on a solid surface such as a nitrocellulose or nylon membrane or a glass plate.

Fluorescent markers are typically added to the target in one of two ways: (i) fluorescent nucleotide bases are used when making the cDNA copy of the mRNA or (ii) biotinylated nucleotides are first incorporated, followed by an application of fluorescent marker-labeled streptavidin, which will bind to biotin (S. Kohane "Microarrays for integrated genomics" MIT Press, 2002).

Depending on manufacturer specific protocols, the target-probe hybridization process on a microarray typically occurs over several hours. All unhybridized targets are then washed off and the microarray is illuminated with laser light and scanned using laser confocal microscopy. A digital image scanner records the brightness level at each grid location on the micro-array corresponding to particular probe species. The brightness level is correlated with the absolute amount of mRNA in the original sample, and by extension, the expression level of the gene associated with this mRNA.

DNA and protein micro-array technology has yet to be successfully developed into monolithically integrated single chip devices that conveniently and inexpensively capture, deliver and interpret information. What is currently understood by the term "biochip" is typically a glass slide with an array of detection regions, each region containing specific probe molecules, which requires complex and bulky equipment for external laser excitation, scanning and imaging of the optical signals. In addition to the cost associated with this equipment, there is also a requirement for it to be operated by highly trained and skilled personnel in order to ensure error free interpretation of the gathered data and troubleshooting. These limitations of cost and space associated with the present status of biochip technology currently prevent DNA and protein analysis from finding a wider use in hospital, point-of-care, and limited resource settings.

Over the past few years there has been some effort deployed to reduce the cost and size of biochips by integrating them with the associated laser excitation and image scanning apparatus (Vo-Dinh et al., "Integrated circuit biochip microsystem" U.S. Pat. No. 6,448,064, September 2002; Duvenecket et al., "Optical detection device based on semiconductor laser array" U.S. Pat. No. 6,469,785, October 2002; Bruno-Raimondi et al "Sensing unit provided with separated detection light guiding" U.S. Pat. No. 6,437,345, August 2002; Neuschafer et al "Sensor platform and method for the parallel detection of a plurality of analytes using evanescently excited luminescence" U.S. Pat. No. 6,078,705, June 2000). These documents proposed an integrated circuit biochip micro system, which combines lasers, detectors, focusing optics and biological sensing elements within a single microassembly. In microelectronics this type of integration is typically defined as hybrid integration, i.e., when individual elements are produced separately by processing a number of separate substrates/wafers and then diced out and microassembled together. Although advantageous over the bulky, bench-top devices, such hybrid integrated biochips still lack the cost and performance advantage of true monolithic integration. In addition, these devices require the use of fluorescent markers which unnecessarily complicates the analysis procedure and which ideally should be avoided in a simple point-of-care device.

An optoelectronic biochip sensor has previously been proposed using light sources for determining a molecular recognition event on the basis of monolithically integrated dielectric waveguide components (Bazylenko et al., "Integrated circuit biochip microsystem" U.S. Pat. No. 7,768,650 issued Aug. 3, 2010). While such sensors will typically meet sensitivity requirements for useful sensors, their dimensions are limited by diffraction effects in the dielectric waveguide components used. Such sensors can therefore be less attractive for integration with silicon based electronic components, such as complementary metal oxide semiconductor (CMOS) circuits, which are many times smaller.

Excitations which do not exhibit the disadvantages associated with using light sources to determine a specific binding event are so-called surface plasmons polaritons or plasmonic mode excitations, i.e., electromagnetic excitations at a metal-dielectric interface. These excitations may be guided using structures that are much smaller than the wavelength of photons of the same frequency. Discrete devices for generating such plasmons are known for example from the article by Walters et al., "A silicon-based electrical source of surface plasmon polaritons", Nature Materials, 6 December 2009. Such plasmonic mode excitations provide an opportunity to develop methods and devices configured to utilize plasmonic sources to determine molecular recognition events.

Surface plasmon resonance (SPR) measurement systems can be used to detect shifts in refractive indices of samples associated with SPR sensors that are included in the systems. A conventional SPR measurement system includes an external light source that illuminates an SPR sensor through an input optical path that typically includes a prism. Light reflected by the SPR sensor propagates through an output optical path and is intercepted by a detector. The optical paths typically include telescopes, polarizers, acousto-optic deflectors, and other optical components that add complexity to the SPR measurement systems, especially when the SPR sensor includes an array of sensing elements. To accommodate an array of sensing elements, the output optical path includes an imaging system that maps each sensing element in the array to a corresponding detection element within the detector. The imaging system can increase the manufacturing cost of the SPR measurement system and can limit the physical density of the sensing elements in the array due to the limited registration that can be achieved by a typical imaging system. An opto-electric SPR biosensor that is illuminating from below through a supporting substrate wafer is known from Bahl et al., "Integrated Opto-electric SPR Sensor", US 2007/0052049 A1, Mar. 8, 2007. The biosensor of Bahl et al. suffers from fragility due to the prismatic coupling structures that are etched into the substrate and limited integration density due to the ray optics principles that guide the design.

A further known limitation of the conventional SPR technique is its relatively low sensitivity, which is typically between $10^{-3}$ and $10^{-5}$ refractive index units (RIU) although the sensitivity can, in some circumstances, be improved up to $10^{-6}$ RIU. However, for modern demanding bio-chemical applications, a sensitivity of about $10^{-9}$ RIU or better is essential. Thus, a more advanced SPR technique has been applied in bio-chemical sensors. This more advanced SPR technique is based on the application of the Goos-Hanchen (GH) effect. In some sensors, the GH effect is small and not useful for sensing measurements. In other sensors, the GH effect is more substantial and is used to improve evanescent-wave propagation. Advanced biosensors exploiting GH effect phenomena associated with plasmonic mode excitations are known for example from Potyrailo et al., "Methods and systems for detecting biological and chemical materials on a submicron structured substrate", US 2008/0280374 A1, Nov. 13, 2008. However these proposed biosensors are not monolithically integrated and thus require bulky and expensive external equipment for the scanning and imaging of optical signals generated by the fluorescent markers.

BRIEF SUMMARY

The subject matter described herein includes integrated plasmonic sensing devices and associated measurement apparatus for said integrated plasmonic sensing devices, as well as practical and cost-effective methods of manufacturing said integrated plasmonic sensing devices. In certain embodiments, the subject matter described herein relates to monolithically integrated plasmonic sensing devices that can provide label-free detection (eliminating the need to use fluorescent or absorbing markers) and in-situ monitoring of conditions at each detection region. Using the described methods and devices, cost/performance ratio reductions can be achieved over discrete element microassembly devices and over monolithically integrated optoelectronic biochips that rely on optical means of determining a molecular recognition event, opening the way for the widespread use of inexpensive systems for measuring biochemical reactions involving oligonucleotides, proteins, and small molecules.

In the embodiments described herein, a detection region is formed on the surface of one or more interaction regions, i.e. regions where the surface plasmon excitation modes interact with the material under test, including a first metal layer, a plasmonic scattering feature of a second metal layer, and/or second metal layer in the via region, so that the electromagnetic fields of plasmonic mode excitations interact with the substance under test. In some embodiments, the detection region comprises organic/inorganic molecules/polymers tethered through covalent or non-covalent interactions to the aforementioned metals that are capable of selective interaction with a target molecule.

In one embodiment described herein, an integrated plasmonic sensing device for testing substances includes a plurality of detection regions and a plasmonic backplane disposed over a monolithically integrated image sensor. The plasmonic backplane includes at least one plasmonic scattering region and at least one plasmonic via region, the plasmonic scattering region including at least a portion of a first metal layer, the plasmonic via region including at least a portion of the first metal layer and at least a portion of a second metal layer above the first metal layer, and the plasmonic via region further including a dielectric layer between the portion of the first metal layer and the portion of the second metal layer. As used herein, a plasmonic backplane disposed on a monolithically integrated image sensor refers to an integrated plasmonic sensing device produced by processing a substrate comprising a functional image sensor, for example a commercially available image sensor such as a charge coupled device (CCD), an array of photodiodes including avalanche photodiodes, or a complementary metal oxide semiconductor (CMOS) sensor array, in a sequence of deposition, photolithography, etching, imprint lithography, and/or chemical mechanical polishing (CMP) steps as opposed to hybrid integration which involves processing a number of (two or more) substrates and then aligning and attaching together the devices produced from those substrates. In another embodiment the image sensor can be realized as semiconductor thin film photodetectors and in this case a lower cost non-semiconductor substrate (e.g., glass substrate) can be used, making this embodiment a potentially more cost effective option as compared to the use of a semiconductor substrate. A semiconductor polymer can be used as a semiconductor thin film material. Alternatively, an inorganic semiconductor thin film material such as GaN or amorphous or polycrystalline silicon could be used as a thin film photodetector. A desirable feature of monolithic integration is that components of the device can be aligned to each other using photolithographic alignment means i.e., by reading alignment marks formed on the substrate in predetermined locations at the initial stages of the device fabrication. Monolithic integration with an image sensor uses processes to fabricate the plasmonic backplane that are compatible with the underlying image sensor and do not compromise the function of said image sensor. For example, such processes can be carried out at temperatures not exceeding approximately 425 degrees Celsius and etching processes can be designed to reduce eroding existing electrodes used to contact the image sensor.

In further embodiments, the plasmonic scattering region includes a plurality of plasmonic scattering features and/or the plasmonic via region includes a plurality of plasmonic scattering features. These features are designed to direct the propagation of plasmonic mode excitations and may be related by analogy to distributed antenna arrays in which electromagnetic waves can be directed at microwave and radio frequency ("RF") frequencies. A difference between an arrangement of plasmonic scattering features that directs the propagation of plasmonic mode excitations and an antenna array that directs the propagation of electromagnetic waves is the much smaller dimensions (typically sub-micrometer) of the plasmonic scattering features, in proportion to the much shorter effective wavelengths of the plasmonic mode excitations to be directed in comparison to the wavelengths of microwave or RF electromagnetic waves. Another difference is the modified linear response of materials at high frequencies (typically several hundred terahertz), as typically described by the complex frequency-dependent permittivity. In designing such an arrangement of plasmonic scattering features, models that approximate the frequency-dependent permittivity at design frequencies based on published data (e.g. "Handbook of optical constants of solids III", edited by Edward D. Palik, Academic Press, (1998).) or based on measured values (e.g. values measured using thin-film variable angle spectral ellipsometry as known in the art) can be utilized. Using such models the propagation of plasmonic mode excitations can be simulated in two or in three spatial dimensions using known finite difference or finite integral techniques and performance modified through variations in feature geometry and arrangement geometry.

For example, an arrangement of plasmonic scattering features in a plasmonic scattering region can comprise nine cylindrical gold features with diameter of 160 nanometers and height of 50 nanometers on a square 3×3 grid with typical nearest neighbor separation distance of 80 nanometers and an arrangement of plasmonic scattering features in a plasmonic via region can comprise nine cylindrical gold features with diameter of 80 nanometers and height of 50 nanometers on a square 3×3 grid with typical nearest neighbor separation distance of 160 nanometers when seeking power transmission through a plasmonic backplane to the underlying image sensor when the wavelength of the incident light is approximately 780 nanometers, the angle of incidence is approximately 50 degrees, and the incident light is polarized along a row or column of the square 3×3 grid arrangement of plasmonic scattering features, when the plasmonic backplane further comprises a dielectric interlayer formed of 100 nanometers of silicon oxide. More generally, the arrangement of plasmonic scattering features can be periodic, quasiperiodic, or aperiodic and can comprise one or more plasmonic scattering features.

In a further embodiment of the disclosed subject matter, the plasmonic scattering features of the plasmonic scattering region are formed from the same material as the second metal layer, typically gold, silver, aluminum, copper or alloys thereof. For example, when the second metal layer is gold, a patterning step can simultaneously create arrangements of gold plasmonic scattering features in the plasmonic scattering regions. This provides a simplified fabrication process flow in comparison to fabrication processes that use two metallization processes to separately form the second metal layer of the plasmonic via regions and the plasmonic scattering features in the plasmonic scattering regions. Using this technique the plasmonic scattering features are formed of the same material as the second metal layer and have a feature thickness similar to the thickness of the second metal layer.

In a further embodiment, the plasmonic scattering features have a footprint selected from the group consisting of round, square, ellipsoid and rectangular. These shapes can be formed using, for example, imprint lithography techniques such as described in the article by Ferry, et al., "Light trapping in ultrathin plasmonic solar cells," Optics Express, Vol. 18, No. 102, Jun. 21, 2010. The aspect ratio (feature height to feature width) of the plasmonic scattering features can be as large as 3:1 but is preferably less than one.

In a further embodiment, the plasmonic scattering features of the plasmonic via region are formed from the same material as the first metal layer, typically gold, silver, aluminum, copper or alloys thereof. For example, when the first metal layer is gold, a patterning step can simultaneously create arrangements of gold plasmonic scattering features in the plasmonic via regions. This provides a simplified fabrication process flow in comparison to fabrication processes that use two metallization processes to separately form the first metal layer of the plasmonic scattering regions and the plasmonic scattering features in the plasmonic via regions. Using this technique the plasmonic scattering features are formed of the same material as the first metal layer and will have a feature thickness similar to the thickness of the first metal layer.

In further embodiments, the plasmonic scattering region includes a metallic nanoparticle tethered to the first metal layer and/or the plasmonic scattering region includes a metallic nanoparticle tethered to a plasmonic scattering feature of the second metal layer and/or the plasmonic via region includes a metallic nanoparticle tethered to the second metal layer. In metallic nanoparticles, an incident electromagnetic wave can couple to the conduction electrons of the metal, exciting a localized surface plasmon, as described for example, by Raether in "Surface-plasmons on smooth and rough surfaces and on gratings." Springer Tracts in Modern Physics. 1988; 111:1-133. For example, gold and silver nanoparticles with radii much smaller than the wavelength of light strongly scatter visible light, with extinction, absorption, and scattering cross-sections that can be orders of magnitude larger than the particle's physical cross-section. Correspondingly, the local fields surrounding the particles can be significantly enhanced compared to the incident electromagnetic field. The specific absorption and scattering properties of plasmonic nanoparticles are dependent on their size, shape, composition, and charge density, as well as the refractive index of the surrounding medium. The dependence of nanoparticle plasmon resonances on the local dielectric environment has been previously exploited for applications in biomolecular detection, as described for example in the article by Lal et al., "Nano-optics from sensing to waveguiding." Nature Photonics. 2007; 1:641-8. Similarly, nanoparticle dimer pairs with interparticle separations of a few nanometers have been used for detection of oligonucleotide hybridization events, as described for example in the article by Sonnichsen, et al., "A molecular ruler based on plasmon coupling of single gold and silver nanoparticles." Nature Biotechnology. 2005; 23(6):741-5. When the plasmonic scattering region includes a metallic nanoparticle tethered to the first metal layer, the geometry resembles a point dipole above a conducting sheet—an electromagnetic problem formally equivalent to a system of two dipoles in the electrostatic limit: the original nanoparticle and it's "image" charge or particle, as described for example in the article by Le et al., "Plasmons in the metallic nanoparticle—Film system as a tunable impurity problem." Nano Letters. 2005; 5(10):2009-13. Consequently, the metallic nanoparticle tethered to the first metal layer forms a system that is similar in behavior to a nanoparticle dimer system, but with the added advantages of fabrication process compatibility and scalability. The thickness of the first metal layer can be selected to support strongly localized electromagnetic coupling between the film and particle, inducing an antenna-like response. Similarly, the diameter of the nanoparticle, which may be a gold nanoparticle, can be selected to be large enough to produce strong dipolar scattering with high albedo and small enough to suppress higher order quadrupolar resonances. Large changes in scattering efficiency resulting from changes in the separation distance between the metal nanoparticle and the first metal layer can be readily exploited for detection of DNA hybridization events by inducing changes in the overall transmission efficiency of the plasmonic backplane.

In a further embodiment, the plasmonic scattering region includes a luminescence catalyst tethered to the first metal layer and/or the plasmonic scattering region includes a luminescence catalyst tethered to a plasmonic scattering feature of the second metal layer and/or the plasmonic via region includes a luminescence catalyst tethered to the second metal layer. The luminescence catalyst may comprise an enzymatic bioluminescence system, such as a luciferase system, a fluorescence system, such as a quantum dot system (e.g., CdSe quantum dots), an organic fluorophore system (e.g., fluorescein), a fluorescent protein system (e.g., green fluorescent protein (GFP)), or a chemiluminescence system, such as a horseradish peroxidase system. The design of the plasmonic backplane can be optimized for operation at the excitation and/or de-excitation frequency of the luminescence catalyst system used. For example, the dimensions and arrangement of the plasmonic scattering features can be selected to transfer power efficiently through the plasmonic backplane at the de-excitation frequency of the luminescence catalyst system while rejecting power at the excitation frequency. In a further example, the dimensions and arrangement of the plasmonic scattering features can be selected to enhance the local electromagnetic field intensity at the location of the luminescence catalyst.

In a second aspect of the subject matter described herein, there is provided a method of manufacturing an integrated plasmonic sensing device comprising steps of cleaning or otherwise preparing an image sensor substrate, forming a patterned metal layer using a sequence of lithography, deposition, polishing and/or etching steps, forming a patterned dielectric interlayer using a sequence of lithography, deposition, and/or etching steps, and then forming a second patterned metal layer using a sequence of lithography, deposition, polishing and/or etching steps. In this method the plasmonic scattering regions and plasmonic via regions and any plasmonic scattering features can be aligned to each other. The method can further comprise steps of (i) forming a first metal layer over the image sensor; (ii) forming a dielectric layer over the first metal layer; (iii) forming a second metal layer over the dielectric layer; and (iv) forming a plurality of plasmonic scattering features in the first metal layer and the second metal layer. The individual devices may then be diced out from the substrate and wire-bonded into packages. The entire packaged device could be disposed after use.

In a third aspect of the subject matter described herein there is provided a method of testing a substance comprising steps of disposing the substance over a detection region of an integrated plasmonic sensing device that includes an integrated image sensor and plasmonic backplane, receiving incident light onto the substance, varying the illumination conditions in time, including one or more of the polarization state, angle of incidence, wavelength, and illumination intensity, detecting energy transmitted through the backplane to the image sensor, generating an image sensor signal based on the transmitted energy, and determining the occurrences of molecular recognition events at the detection region based the signals received from the image sensor. Such method can be carried out using a single disposable integrated plasmonic sensing device and a suitable illumination apparatus.

When methods described herein are implemented using plasmonic sensing devices of the type described herein that include multiple detection regions, the methods can advantageously allow for individual monitoring of the conditions at each detection region based on the signals received by the image sensor containing information about the status of molecular recognition at each detection region. The information contained in the signals received by the image sensor can be derived from a change in refractive index, or from a change in intensity of light emitted by fluorescent markers, or from a change in attenuation induced by absorption markers.

A further feature of the methods described herein is that detection regions prior to the disposing of the substance therein can undergo individual testing. The testing data can be stored and used for interpretation of the information received from the corresponding detection regions during molecular recognition in order to reduce errors in determining a molecular recognition event. During the testing and monitoring processes, the illumination intensity can be modulated at a certain frequency and the electrical output signal can then be filtered out at that frequency to improve signal to noise ratio.

The detecting step can further comprise in-situ detection on the basis of a change in the signals received at the image sensor caused by the molecular recognition event. For example, the signals received at the image sensor can result from illuminating light being modified by several mechanisms including: a refractive index change associated with a molecular recognition event, luminescence associated with a molecular recognition event, or absorption associated with a molecular recognition event.

By monitoring the signals received by the monolithically integrated image sensor, the entirety of the detection regions can be measured repeatedly during the molecular recognition process until no further change is observed in the image sensor signal, corresponding to steady-state conditions at the detection regions. This allows for monitoring of molecular recognition conditions at each detection region individually as a function of time as well as illumination condition.

The embodiments of an integrated plasmonic sensing device described herein can be disposed of as a single device after the testing is completed, thus avoiding risk of cross contamination which may become an issue when certain parts of microassembly devices have to be reused, e.g., when only the microarray part is designed to be disposable.

An integrated plasmonic sensing device in accordance with the present description can further comprise a fluidic chamber in fluid communication with the plurality of detection regions for delivering the substance under test. This chamber can include pumping means to flow the liquid under test along the plurality of detection regions. This fluidic chamber can also be monolithically integrated with the integrated plasmonic sensing device by appropriate processing steps. In one alternative, this integrated fluidic chamber can be made of microimprinted or molded polymeric layers.

Among techniques for determining a molecular recognition event, a plasmonic electromagnetic field detection method in accordance with the present description has the advantage that the plasmonic mode excitations interact only with probe-target molecular constructs that are close to the plasmonic waveguide surface.

In some applications of the plasmonic sensing devices and methods described herein, fluorescent markers are utilized. In this context, another embodiment of the integrated plasmonic sensing devices allows for testing substances marked with one or more fluorescent markers. In such integrated plasmonic sensing devices the plasmonic scattering features are tuned to the excitation wavelengths of the corresponding fluorescent markers and/or the detectors of the image sensor are tuned to the excitation or emission wavelength of the corresponding fluorescent marker. The wavelength tuning can be achieved for example by adjusting the material composition, geometry, or arrangement of the respective plasmonic scattering features as was described earlier. More than one fluorescent marker with absorption bands and emission bands at different wavelengths could be used in the same detection region when the illumination wavelength is changed.

Other embodiments use absorption markers as opposed to fluorescent markers. According to these embodiments the absorption markers are attached to the molecules of the substance under test. Absorption markers with absorption bands at different wavelengths could be used in the same interaction region. More than one type of absorption markers with absorption bands at different wavelengths could also be used. The electromagnetic field of the plasmonic mode excitations propagating in the interaction region interacts with the absorption markers attached to target molecules bound through covalent or non-covalent interactions in the vicinity of the interaction region, which causes a reduction in the intensity of plasmonic mode excitations transmitted through the plasmonic backplane proportional to the amount of target molecules bound through covalent or non-covalent interactions. This reduction in intensity may be registered as a reduction in intensity at the image sensor.

It can be beneficial to eliminate the use of markers (e.g., fluorescent or absorbent markers) in determining a molecular recognition event. Such marker-free recognition detection can be achieved by registering a change in refractive index resulting from molecular recognition events. According to these embodiments, the electromagnetic field of the plasmonic mode excitation interacting with a layer of target molecules bound at the interaction region changes the effective refractive index in the vicinity of the interaction region, which modifies the effective wavelength or propagation constant of the supported plasmonic modes. A number of embodiments described herein detect such change in refractive index associated with the marker-free recognition event by translating it into a change in the plasmonic mode excitation intensity decoupled from the interaction region onto the image sensor.

To reduce noise due to fluctuations in temperature during in-situ monitoring of the status of marker-free recognition, each detection region could further contain one or more reference interaction regions which are identical to those used to monitor marker-free recognition events but which do not have surface-bound target molecules. By using the one or more reference interaction regions a change in refractive index resulting from a change in the temperature of the detection region or the temperature of the chip as a whole could be separated from the change in refractive index resulting from a marker-free recognition event.

In all relevant embodiments, the intensity of the illumination source can be modulated at a certain frequency and this frequency can then be filtered out from the corresponding image sensor signals in order to improve signal to noise ratio at each detection region. Additionally, when fluorescent markers are used, such modulation can provide information about the characteristic fluorescent decay time which in turn can provide additional information about the molecular recognition process.

In further embodiments, a plasmonic sensing device includes a plasmonic backplane disposed on a monolithically integrated image sensor. The plasmonic backplane has a plasmonic scattering region including at least a portion of a first metal layer. The plasmonic backplane also has a plasmonic via region including at least a portion of the first metal layer, at least a portion of a second metal layer above the first metal layer and a dielectric layer between the portion of the first metal layer and the portion of the second metal layer. In accordance with these embodiments, at least a portion of the plasmonic scattering region does not overlap the plasmonic via region. In other words, the plasmonic scattering region is laterally offset from the plasmonic via region.

Methods of making the plasmonic sensing devices of the type described in the preceding paragraph include the steps of forming a first metal layer over the image sensor, forming a dielectric layer over the first metal layer, and forming a second metal layer over the dielectric layer. In accordance with the described methods, a plurality of plasmon vias are formed in the first metal layer and a plurality of plasmonic scattering features are formed in the first metal layer and the second metal layer. At least some of the resulting plasmonic scattering features in the second metal layer do not overlap any of the plurality of plasmon vias.

Other embodiments relate to methods of determining a property of incident light that include the step of receiving the incident light onto a plasmonic sensing device that includes an integrated image sensor and a plasmonic backplane. The plasmonic backplane is disposed on a monolithically integrated image sensor and includes a plasmonic backplane having a plasmonic scattering region and a plasmonic via region. The plasmonic scattering region includes at least a portion of a first metal layer and the plasmonic via region includes at least a portion of the first metal layer and at least a portion of a second metal layer above the first metal layer with a dielectric layer between the portion of the first metal layer and the portion of the second metal layer. In these embodiments, at least a portion of the plasmonic scattering region does not overlap the plasmonic via region. The described methods further include the step of varying an illumination condition of the incident light and guiding plasmonic modes in a lateral direction from the plasmonic scattering region to the plasmonic via region. Energy transmitted through the plasmonic via region to the image sensor is detected and an image sensor signal based on the detected energy is produced. This image sensor signal is detected and the property of the incident light is determined using the image sensor signal.

The subject matter described herein also relates to inexpensive, disposable sensor devices that can be interfaced directly to a computer and be available to clinical environments both in terms of cost and skills required to operate it. Towards that goal, embodiments described herein simplify the DNA and protein analysis procedure by removing the need for the use of fluorescent markers in detecting molecular recognition events and/or removing washing steps. In addition, for research and diagnostic purposes as well as to reduce possible errors in determining a molecular recognition event the embodiments described herein enable continuous monitoring of the conditions at each measurement region during molecular recognition.

The subject matter described herein includes monolithically integrated plasmonic sensor devices, as well as practical and cost effective methods of their manufacture. In certain embodiments, the subject matter described herein relates to plasmonic sensors that can provide marker-free detection (eliminating the need to use fluorescent markers) and in-situ monitoring of conditions at each measurement region. Using the described methods and devices, cost/performance ratio reduction can be achieved over discrete element microassembly devices and over monolithically integrated optoelectronic biochips that rely on optical means of determining a molecular recognition event, opening the way for the widespread use of inexpensive, disposable DNA and protein chips. In exemplary embodiments, the plasmonic sensing devices can be biochips.

In embodiments described herein, a sensor for testing biological or non-biological substances includes a plurality of the plasmonic sensing devices described above. For example, in accordance with embodiments described here, a sensor for testing biological substances includes a plurality of measurement regions, a plasmonic device configured to determine a molecular recognition event at each measurement region, wherein the plurality of measurement regions and the plasmonic device are monolithically integrated into a single chip which is electrically powered and produces electrical signals in response to molecular recognition events at each measurement region. As used herein, the term "monolithically integrated chip" refers to a chip produced by processing one substrate in a sequence of deposition, photolithography, etching, imprint lithography, and/or chemical mechanical polishing steps as opposed to hybrid integration which involves processing a number of (two or more) substrates and then aligning and attaching together the chips produced from those substrates. Another feature of monolithic integration is that all components of the chip can be aligned to each other using photolithographic alignment means i.e., by reading alignment marks formed on the substrate in predetermined locations at the initial stages of the chip fabrication.

The sensor can be arranged so that electrical signals in response to the molecular recognition events at each measurement region are induced sequentially over the entire plurality of the measurement regions so that only one measurement region is monitored at a time. This sequence of individual testing of the entirety of the measurement regions can be repeated during the molecular recognition process until no further changes in the conditions at the measurement regions are detected. This allows for monitoring of molecular recognition conditions at each measurement region individually as a function of time. Such individual testing also reduces the cross-talk from one measurement region to another as well as the general noise floor or background intensity level.

The embodiments of a monolithically integrated sensor described herein can be disposed of as a single device after the testing is completed, thus avoiding risk of cross contamination which may become an issue when certain parts of microassembly devices have to be reused, e.g., when only the microarray part is designed to be disposable.

In embodiments of monolithically integrated sensors described herein, determining a molecular recognition event can be carried out by a plurality of electrically driven sources of surface plasmon polaritons ("plasmonic source") and a plurality of photodetectors. For example, one plasmonic source and one photodetector can be associated with each measurement region. Alternatively, more than one plasmonic source and/or more than one photodetector can be associated with each measurement region, one plasmonic source can be associated with more than one photodetector, or more than one plasmonic source can be associated with one photodetector. In addition, more than one measurement region can be associated with one photodetector.

Sensors including a plasmonic source can further comprise a fluidic chamber attached to the plurality of measurement regions for delivering the biological substance under test. This chamber can have pumping means to flow the liquid under test along the plurality of measurement regions. This fluidic chamber can also be monolithically integrated with the sensor by appropriate processing steps. In one alternative this integrated fluidic chamber can be made of micro-imprinted or molded polymeric layers.

In order to enable control and monitoring of conditions at each measurement region sensors can further comprise a first plurality of electrical controls for individually controlling each plasmonic source within the plurality of the plasmonic sources and a second plurality of electrical controls for individually controlling each photodetector within the plurality of the photodetectors. Such electrical controls can comprise a plurality of electrodes to deliver the drive current to the plasmonic sources and to receive electrical signals from the photodetectors. These electrodes can be implemented as multilayer metallization with interlayer dielectric layers located between the metal layers located on top of each other. If required, appropriate planarization steps can be used to ensure a flat (planar) finished surface of the multilayer metallization stack.

For sensors comprising a plurality of plasmonic sources and a plurality of photodetectors as a means for determining a molecular recognition event, there are a number of embodiments in which the sensor can be realized. In the first such embodiment the sensor can be fabricated on a semiconductor (e.g., silicon) substrate and the photodetectors can be formed on that substrate. In this case the photodetectors can be formed as either a charge coupled device (CCD), as photodiodes including avalanche photodiodes, or as complementary metal oxide semiconductor (CMOS) sensors. In the second embodiment the photodetectors can be realized as semiconductor thin film photodetectors and in this case a lower cost non-semiconductor substrate (e.g., glass substrate) can be used, making this embodiment a more cost effective option as compared to the use of a semiconductor substrate. A semiconductor polymer can be used as a semiconductor thin film material. Alternatively, an inorganic semiconductor thin film material such as GaN or amorphous or polycrystalline silicon could be used as the thin film photodetector.

Similarly to the embodiments described above in relation to the photodetectors, the plasmonic sources can also be implemented on either a semiconductor substrate (e.g., silicon) or on lower cost non-semiconductor substrate (e.g., glass substrate). For example, organic plasmon-emitting diodes can be implemented as plasmonic sources as described in article by Koller, et al., "Organic plasmon-emitting diode", Nature Photonics, Sep. 28, 2008.

Among techniques for determining a molecular recognition event, a plasmonic electromagnetic field excitation method can have the advantage that the plasmonic mode excitations interact only with probe-target molecular constructs that are close to the plasmonic waveguide surface.

Within the scope of the present disclosure, plasmonic mode excitation interaction regions ("interaction regions") are monolithically integrated with the plasmonic sources, typically on a plasmonic backplane, and the plasmonic backplane is in turn monolithically integrated with the photodetectors. The measurement region is formed on the surface of one or more interaction regions so that the electromagnetic fields of plasmonic mode excitations interact with the biological substance under test. This interaction region can be made of nanostructured metals such as gold, silver, copper, aluminum, or alloys of such materials. The measurement region comprises organic/inorganic molecules/polymers tethered through covalent or non-covalent interactions to the aforementioned metals that are capable of selective interaction with a target molecule.

In some sensor applications the use of more than one type of fluorescent markers is required. In this context another embodiment of the sensors allows for testing biological substances marked with one or more fluorescent markers. In such sensors there is more than one plasmonic source associated with each interaction region and/or more than one detector associated with each interaction region. The plasmonic sources and/or photodetectors associated with each interaction region can operate at different wavelengths. The plasmonic sources can be tuned to the excitation wavelengths of the corresponding fluorescent markers and the detectors can be tuned to the emission wavelength of the corresponding fluorescent markers. The wavelength tuning can be achieved for example by adjusting the material composition of the respective plasmonic sources and photodiodes as was described earlier or by adjusting the geometry of the plasmonic mode excitation filtering regions and/or the encapsulating dielectric layers.

Other embodiments use absorption markers as opposed to fluorescent markers. According to these embodiments the absorption markers are attached to the molecules of the biological substance under test. Absorption markers with absorption bands at different wavelengths can be used in the same interaction region. More than one type of absorption markers with absorption bands at different wavelengths can also be used. The electromagnetic field of the plasmonic mode excitations propagating in the interaction region interacts with the absorption markers attached to target molecules bound through covalent or non-covalent interactions in the vicinity of the interaction region, which causes a reduction in the intensity of plasmonic mode excitations transmitted through the interaction region proportional to the amount of target molecules bound through covalent or non-covalent interactions. This reduction in intensity is received by a photodetector and used to determine a molecular recognition event at the interaction region.

It certain implementations it is beneficial to eliminate the use of markers (e.g., fluorescent or absorbent markers) in determining a molecular recognition event. Such marker-free recognition detection can be achieved by registering a change in refractive index resulting from molecular recognition events. The electromagnetic field of the plasmonic mode excitation interacting with a layer of target molecules bound at the interaction region changes the effective refractive index in the vicinity of the interaction region, which modifies the effective wavelength or propagation constant of the supported plasmonic modes. A number of embodiments described herein detect such change in refractive index associated with the marker-free recognition event by translating it into a change in the plasmonic mode excitation intensity decoupled from the interaction region onto the photodetector.

To reduce noise due to fluctuations in temperature during in-situ monitoring of the status of molecular recognition, each measurement region can further contain one or more reference interaction regions which are identical to those used to monitor marker-free recognition events but which do not have surface-bound target molecules. By using the one or more reference interaction regions a change in refractive index resulting from a change in the temperature of the measurement region or the temperature of the chip as a whole can be separated from the change in refractive index resulting from a marker-free recognition event.

To better utilize the plasmonic mode excitations emitted by a plasmonic source, the plasmonic source can be shared between a number of interaction regions including additional reference interaction regions as described above. In this instance, in some embodiments, though not required, the interaction regions and the reference interaction regions can be arranged symmetrically around the plasmonic source.

In some implementations, different measurement regions within the plurality of measurement regions require different molecular recognition conditions. Therefore, further embodiments propose sensors with a plurality of electrodes to control molecular recognition conditions at each measurement region. Such electrodes could be arranged in a number of layers via a multilevel metallization approach and can be incorporated into the structure during the fabrication. The electrodes can be used to apply voltage to measurement regions to enhance molecular recognition or/and to reduce undesirable interactions, e.g. to remove non-specifically bound molecules via application of an electric field. If the electrodes are arranged in the form of thin film heaters, the current driven through these electrodes can be used to control the temperature individually at each measurement region.

In order to facilitate control of each measurement region, plasmonic source, interaction region, or photodetector, one or more transistors could be formed at each measurement region, plasmonic source, interaction region, or photodetector. If a silicon substrate is used, such transistors can be made using CMOS technology. Alternatively, these transistors can be formed as a thin film transistors, e.g., in amorphous silicon, and incorporated in the sensor structure.

In all relevant embodiments, the intensity of plasmonic mode excitations emitted by the plasmonic sources can be modulated at a certain frequency and this frequency can then be filtered out from the corresponding photodetector signals in order to improve signal to noise ratio at each measurement region. Additionally, when fluorescent markers are used, such modulation can provide information about the characteristic fluorescent decay time which in turn can provide additional information about the molecular recognition process.

In another aspect of the subject matter described herein, there are provided methods of manufacturing sensors comprising steps of forming interaction regions, plasmonic sources, and photodetectors as well as any auxiliary means for determining a molecular recognition event, wherein said plasmonic sources, photodetectors, interaction regions and auxiliary means for determining a molecular recognition event are produced by processing a single planar substrate in a sequence of etching and deposition steps. In these methods the plasmonic sources, detectors, interaction regions and any auxiliary means for determining a molecular recognition event can be aligned to each other. The methods can further comprise steps of (i) forming a first plurality of electrodes; (ii) forming at least one semiconductor layer; (iii) forming a second plurality of electrodes; (iv) forming at least one interaction region; (v) forming a plasmonic mode scattering region; and (vi) forming a plurality of measurement regions on the surface of the interaction regions. The individual sensors may then be diced out from the substrate and wire-bonded into packages. The entire packaged sensor could be disposed after use.

In another aspect of the subject matter described herein there are provided methods of testing a biological or non-biological substance comprising steps of disposing the substance over a plurality of measurement regions, and detecting the occurrences of molecular recognition events at each measurement region. The methods may use a single disposable sensor which is electrically powered and produces electrical signals in response to molecular recognition events at each measurement region. The method can advantageously allow for individual monitoring of the conditions at each measurement region. Such monitoring can comprise generation of plasmonic mode excitations sequentially at each interaction region, interaction of the plasmonic mode excitations with the biological substance, and conversion of the plasmonic mode excitations into electrical signal, said electrical signal containing information about the status of molecular recognition at each of the one or more interaction regions within each measurement region. This information can be derived from a change in refractive index, or from a change in intensity of light emitted by fluorescent markers, or from a change in attenuation induced by absorption markers.

A further advantageous feature of these methods is that interaction regions prior to the disposing of the biological substance can undergo individual testing. The testing data could then be stored and used for interpretation of the information received from the corresponding interaction region during molecular recognition in order to reduce errors in determining a molecular recognition event. In the testing and monitoring process the input plasmonic mode excitations from each plasmonic source can be modulated at a certain frequency and the electrical output signal can then be filtered out at that frequency to improve signal to noise ratio.

Sensors formed in accordance with embodiments described herein include a plurality of measurement regions supporting changes in surface plasmon excitation in response to incident light at each measurement region. The sensors further include a plurality of photodetectors, with each photodetector connected to one or more measurement regions by plasmon vias capable of supporting guided plasmons. The plurality of measurement regions and plurality of photodetectors of these sensors are monolithically integrated and form a sensor capable of producing electrical signals in response to molecular recognition events at each measurement region. In specific embodiments, the photodetectors take the form of an image sensor formed in a semiconductor substrate and the measurement regions form part of a plasmonic backplane located between a fluid chamber and the photodetectors. In certain embodiments, the measurement regions are laterally offset from and connected to one or more photodetectors by plasmon vias. When a fluid chamber is employed, it is formed over the plasmonic backplane and is at least partially transparent to allow incident light directed through the fluid chamber to contact the multiple measurement regions. In accordance with other embodiments, the measurement regions may include tethered molecules for molecular recognition of the biological or chemical substance under test.

The foregoing sensors can be manufactured by methods that provide a substrate including a plurality of photodetectors and monolithically forming a plasmonic backplane over at least some of the plurality of photodetectors. The formed backplane supports plasmonic scattering features defined with a first dielectric layer and first metal layer. The manufacturing methods further include a step of defining plasmon vias that connect the plasmonic scattering features to the plurality of photodetectors. In accordance with these methods, a fluid chamber may be formed over the plasmonic backplane and the photodetectors can be connected to the measurement regions by plasmon vias. According to these methods, the measurement regions may be positioned laterally offset from and connected to the photodetectors by plasmon vias.

In a specific example of a method of manufacturing sensors in accordance with the present disclosure, an image sensor having a plurality of photodetectors is provided and coated with a dielectric material. The dielectric material is stamped to form features in the dielectric material which are coated with a metal to at least in part form a plasmonic backplane having multiple measurement regions with each measurement region having plasmonic scattering features. The methods further include defining plasmon vias that connect the plasmonic scattering features to the plurality of photodetectors of the image sensor.

It is to be understood that, if any prior art publication is referred to herein, such reference does not constitute an admission that the publication forms a part of the common general knowledge in the art in any country.

For the purposes of this specification it is to be understood that the word "comprising" means "including but not limited to", and that the word "comprises" has a corresponding meaning.

It is to be understood that, if any prior art publication is referred to herein, such reference does not constitute an admission that the publication forms a part of the common general knowledge in the art in any country.

For the purposes of this specification it is to be understood that the word "comprising" means "including but not limited to", and that the word "comprises" has a corresponding meaning.

In this specification the term "molecular recognition" is used in a general sense to describe reversible, non-covalent homogeneous or heterogeneous association of two or more molecular species as well as irreversible single or sequential enzymatic or chemical reactions which occur as a result of aforementioned associations. By way of example but not limitation, "molecular species" may include: small molecules such as steroids, fatty acids, monosaccharides, and amino acids; biological polymers such as peptides, proteins, nucleic acids, polysaccharides, and lipopolysaccharides; molecular assemblies including cell membranes, cell walls, and viral capsids.

For the purposes of this specification, it is understood that the word "tethered" includes covalent bonding and non-covalent bonding.

BRIEF DESCRIPTION OF THE SEVERAL VIEWS OF THE DRAWINGS

Embodiments of the subject matter described herein will now be described, by way of example only, with reference to accompanying drawings.

FIGS. 11a-i illustrate a method of manufacturing an integrated plasmonic sensing device in accordance with a second aspect of the subject matter described herein;

FIGS. 20a-k illustrate a method of manufacturing a sensor in accordance with a another aspect of the subject matter described herein; and FIG. 21a-b illustrates a method for testing a biological or non-biological substance in accordance with another aspect of the subject matter described herein.

DETAILED DESCRIPTION

Figure 1:
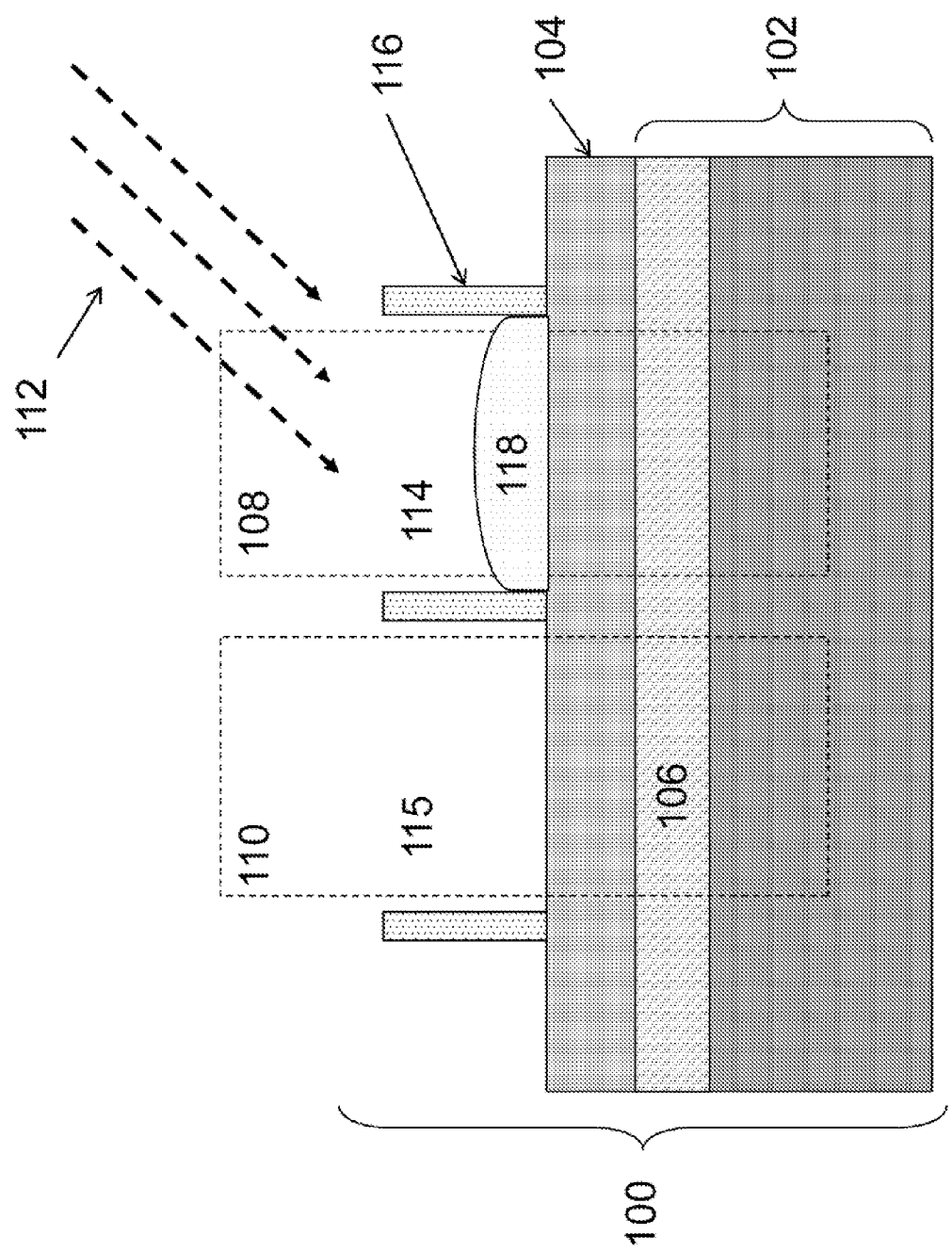
FIG. 1 illustrates a cross-section of a first embodiment of an integrated plasmonic sensing device in accordance with the subject matter described herein utilizing a plasmonic backplane disposed on a monolithically integrated image sensor, and a plurality of fluid containment wells which may contain biological material.

Turning to FIG. 1, there is shown an illustration of a cross-section of a first embodiment of an integrated plasmonic sensing device 100 in accordance with the subject matter described herein utilizing a plasmonic backplane 104 disposed on a monolithically integrated image sensor 102, and a plurality of fluid containment wells 114 and 115 which may contain biological material. In the present disclosure reference is made to biological material and testing of biological material. It should be understood that the present disclosure is not limited to devices and methods for application to biological materials and the present disclosure extends to the application of the devices and methods described herein to non-biological materials. Plasmonic backplane 104 is disposed over image sensor 102, which comprises one or more image sensor pixels 106. The image sensor can be implemented using known processing techniques as an array of photodiodes, as an array of complementary metal oxide semiconductor (CMOS) sensors, or as a charge coupled device (CCD) as described for example in [M. L Adams et al., "Microfluidic integration on detector arrays for absorption and fluorescence micro-spectrometers" Sensor and Actuators, Vol. A104, 2003, pp. 25-31]. Incident light 112 illuminates detection region 108 and adjacent detection region 110, which may comprise fluid containment wells 114 and 115 and underlying regions of the plasmonic backplane 104 and a plurality of the image sensor pixels 106. The fluid containment wells may be separated by well boundaries 116, which can be made of polymeric material such as polydimethylsiloxane (PDMS). The surface of the plasmonic backplane 104 within some of the fluid containment wells may contain a biological substance 118, which may be disposed in the form of a gel or liquid. Biological substance 118 may comprise molecules tethered covalently or non-covalently to plasmonic backplane 104 and may additionally comprise aqueous buffer solutions used to control pH, such as phosphate-buffered saline (PBS), mixtures of solvents used to aid in dissolution such as dimethylsulfoxide, alcohols, or detergents (i.e., SDS, Tween-20), and other untethered organic molecules such as glucose which lie within the detection region 108 or 110. The power coupled through plasmonic backplane 104 and received by the image sensor pixels 106 within a detection region 108 or 110 varies with the illumination conditions, including the angle of incidence, polarization state, wavelength and illumination intensity, as well as the composition of biological material present on the surface of the plasmonic backplane within the detection region.

Typical lateral dimensions of a detection region are in the range of 10 micrometers to 10 millimeters. The thickness of the plasmonic backplane is typically between 100 nanometers and 2 micrometers. The illumination wavelength is typically between 400 nanometers and 1100 nanometers, preferably approximately 780 nanometers. The illumination angle of incidence is typically in the range of −90 degrees to +90 degrees, as measured from the surface normal. The illumination is typically linearly polarized at any angle.

Figure 2:
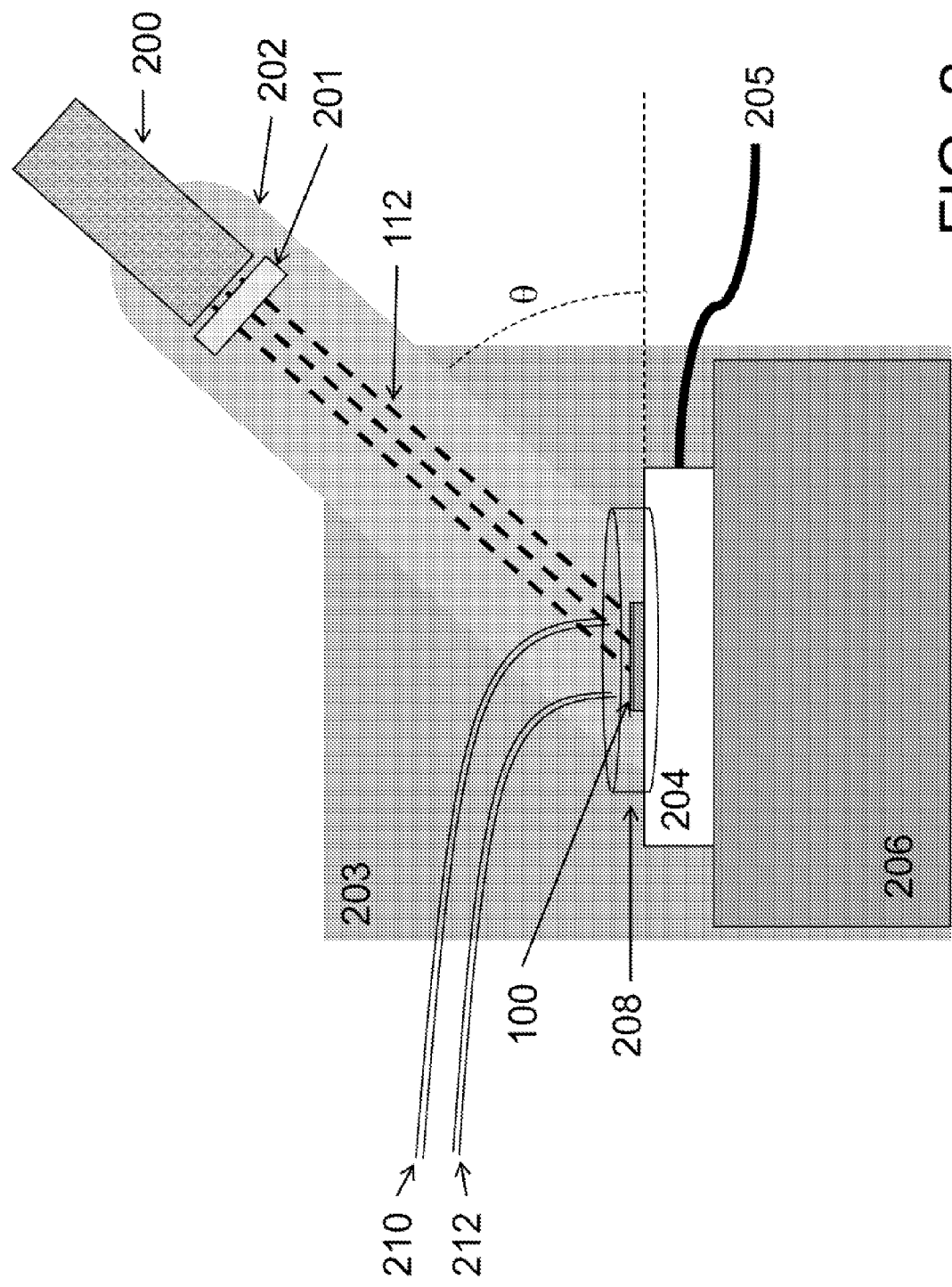
FIG. 2 illustrates schematically an apparatus for controlling the illumination conditions of the incident light in relation to the integrated plasmonic sensing device in accordance with the subject matter described herein.

FIG. 2 illustrates schematically an apparatus for controlling the illumination conditions of the incident light 112 in relation to the integrated plasmonic sensing device 100 in accordance with the subject matter described herein. Light source 200 may comprise a laser, light emitting diode, or fiber coupled light source. In a specific non-limiting embodiment, the light source is selected to provide circularly polarized light at about 780 nanometers in a collimated beam of approximately 1 centimeter in diameter or, alternatively, to provide a wavelength tunable light source in a collimated beam (e.g., a photonic crystal supercontinuum fiber laser with an acousto-optic tunable filter (AOTF)). Polarization filter 201 may then be used to select the desired polarization condition. These components are mounted on illumination arm 202, which rotates to provide the desired angle of incidence. The illumination arm may be balanced by a counterweight to minimize torque at the point of rotation. The electromagnetic power sensed by the integrated plasmonic sensing device can be converted to a digital signal by sensor headboard 204, which may be electrically connected to the removable integrated plasmonic sensing device using a socket or a cartridge connection. The sensor headboard may be connected to a computer system providing data analysis and instrument control by interface cable 205, which may be a universal serial bus (USB) cable. The integrated plasmonic sensor device 100 is located preferably at the point of eucentric rotation of the illumination arm 202. Alignment to the point of eucentric rotation may be provided by an alignment stage 206 capable of translating the integrated plasmonic sensing device 100 and the sensor headboard 204 in one or more dimensions using, for example, micrometer driven crossed roller bearing mechanism linear translation stages. Specimens for analysis may be introduced in solution through fluid input 210 to flow cell 208, which is configured to direct said specimens to the vicinity of the detection regions of the integrated plasmonic sensing device. Effluent waste material from the flow cell can be collected at the output of fluid return 212. An instrument housing 203 may be provided to enclose part or all of the apparatus.

Figure 3:
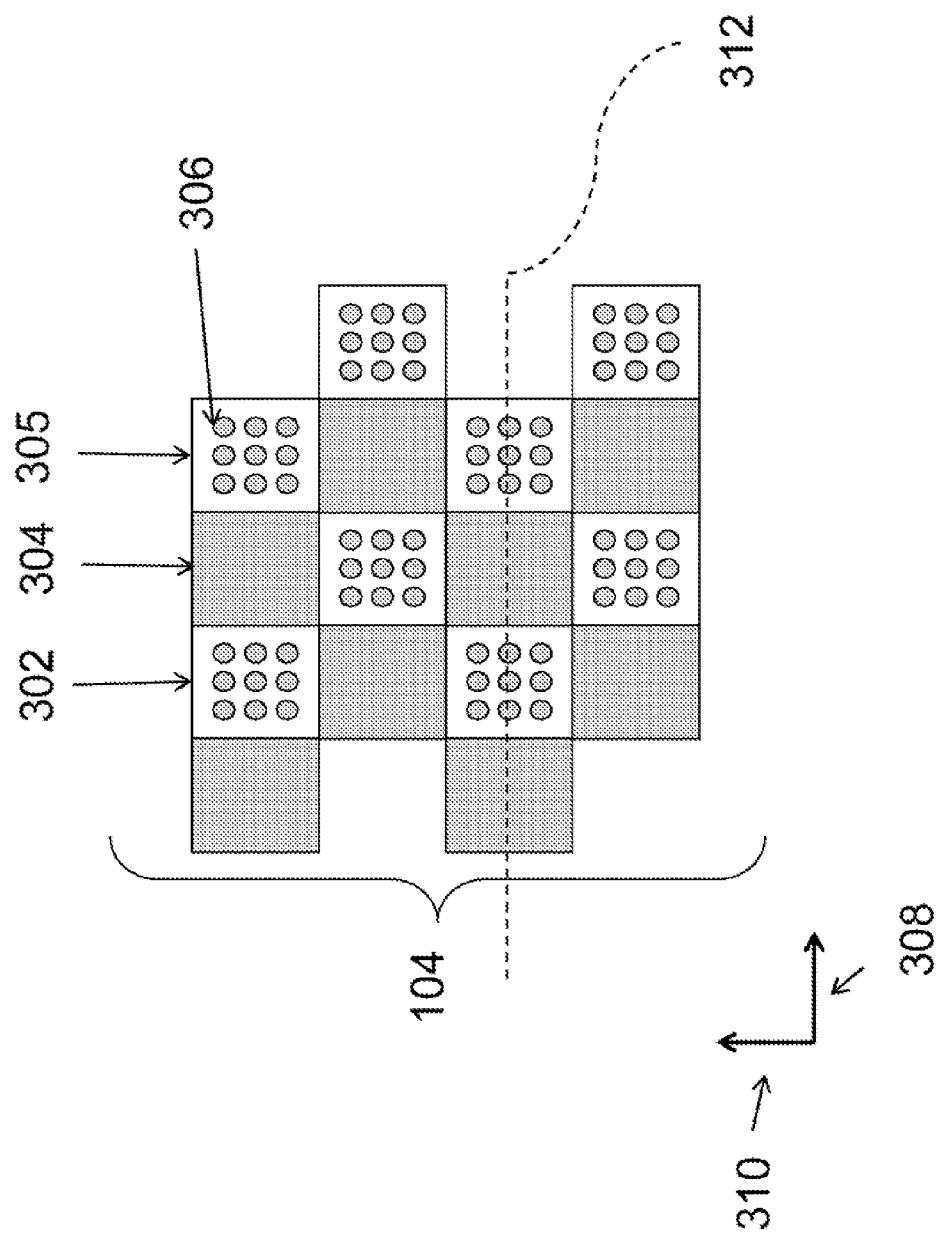
FIG. 3 illustrates a top view of an exemplary embodiment of a plasmonic backplane in accordance with the subject matter described herein.

FIG. 3 illustrates a top view of an exemplary embodiment of a plasmonic backplane 104 in accordance with the subject matter described herein. The plasmonic backplane comprises a checkerboard pattern of plasmonic scattering regions 302 and plasmonic via regions 304 and extends over the surface of each detection region of the integrated plasmonic sensing device in both the x direction 308 and the y direction 310. An adjacent plasmonic scattering region 305 is depicted to the right of plasmonic via region 304. The plasmonic scattering regions comprise arrangements of one or more plasmonic scattering features 306. The dimensions of the plasmonic scattering regions and the plasmonic via regions may be selected in correspondence with one or more of the underlying image sensor pixels 106. In the case that a plasmonic scattering region and/or a plasmonic via region spans an area corresponding to more than one image sensor pixels, the signal from the underlying more than one image sensor pixels can be combined to improve the signal-to-noise ratio, preferably using robust statistical techniques such as median filtering and incorporating an areal weighting function. In another embodiment, the plasmonic scattering region and/or a plasmonic via region dimensions are chosen to correspond to a single underlying image sensor pixel. Exemplary, non-limiting dimensions of the plasmonic scattering region and plasmonic via region are between 500 nanometers and 50 micrometers in the x direction and between 500 nanometers and 50 micrometers in the y direction. In yet another embodiment, the dimensions of the plasmonic scattering region and plasmonic via region are chosen to be large enough to ensure that a region of underlying image sensor pixels near the center of a plasmonic via region can be used as a reference region providing a signal corresponding to an absence of illumination. Cross section 312 is drawn schematically in FIG. 4.

Figure 4:
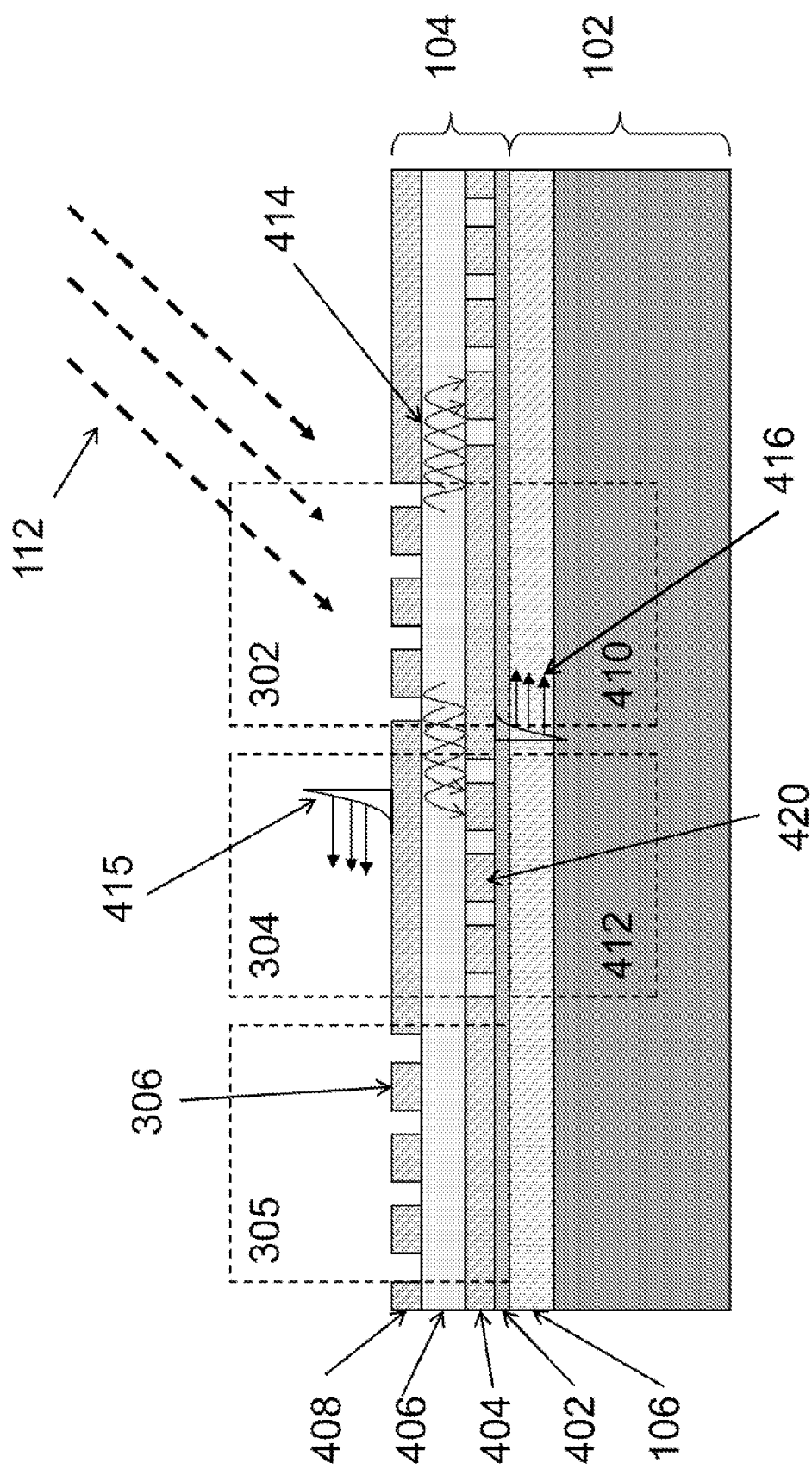
FIG. 4 illustrates schematically a cross section of the exemplary embodiment of a plasmonic backplane of FIG. 3 in accordance with the subject matter described herein.

FIG. 4 illustrates schematically a cross section of the exemplary embodiment of a plasmonic backplane 104 of FIG. 3 and an image sensor 102 in accordance with the subject matter described herein. Plasmonic backplane 104 is disposed upon image sensor 102, which comprises image sensor pixels 106. Plasmonic backplane 104 comprises a diffusion barrier layer 402, which may be made from silicon oxide, over image sensor 102. Metal-I layer 404 is provided over diffusion barrier layer 402. Dielectric interlayer 406 is provided over metal-I layer 404. Metal-II layer 408 is provided over dielectric interlayer 406. The metal layers may be made from gold, silver, copper, aluminum, or alloys of these metals, but preferably of gold or silver. Dielectric interlayer 406 may be made from an oxide or nitride material, preferably silicon oxide. Plasmonic scattering region 302 comprises an arrangement of one or more plasmonic scattering features 306, which may be formed from the same material as metal-II layer 408, and underlying layers of the plasmonic backplane. Plasmonic via region 304 comprises an arrangement of one or more plasmonic scattering features 420 of the plasmonic via region, which may be formed from the same material as metal-I layer 404, and overlying and underlying layers of the plasmonic backplane.

When incident light 112 illuminates backplane 104, it is converted to guided plasmonic modes 414 by the arrangement of one or more plasmonic scattering features 306. The power transferred from the incident light to the guided plasmonic modes varies with the illumination conditions, including the angle of incidence, polarization state, wavelength and illumination intensity, as well as the composition of material in the vicinity of plasmonic scattering region. In some embodiments, power is additionally transferred to surface plasmon polaritons 415 which can then cause interference with the guided plasmonic modes launched at adjacent plasmonic scattering region 305. In this case the power and phase of the surface plasmon polaritons arriving at the adjacent plasmonic scattering region varies with the illumination conditions, including the angle of incidence, polarization state, wavelength and illumination intensity, as well as the composition of material near the surface of the plasmonic via region. Guided plasmon modes 414 are coupled to image sensor pixels underlying the via region 412 by the arrangement of one or more plasmonic scattering features 420 of the plasmonic via region, providing a measurement of the overall power transferred from light source 112 through the plasmonic backplane. The adjacent image sensor pixels of the scattering region 410 provide additional signals which may be interpreted as reference measurements. Note that parasitic internal surface plasmon polaritons 416 may be generated by the arrangement of one or more plasmonic scattering features of the plasmonic via region, but may be largely suppressed by appropriate design. For example, the plasmonic scattering features 420 in the via region 412 may be arranged to provide deconstructive interference for parasitic internal surface plasmon polaritons 416 and/or diffusion barrier layer 402 may comprise a plasmon absorbing material at the interface between diffusion barrier layer 402 and Metal-I layer 404. The plasmon absorbing material may be made from titanium, chromium, palladium, or other transition metals, preferably chromium, and may also function as an adhesion layer for Metal-I layer 404. An exemplary, non-limiting thickness of a plasmon absorbing material layer at the interface between diffusion barrier layer 402 and Metal-I layer 404 are between 1 nanometers and 100 nanometers.

The thickness of the metal-I and metal-II layers may be in the range of 10 nanometers to 1 micron. The thickness of the dielectric interlayer may be between 30 nanometers and 300 nanometers. The thickness of the diffusion barrier layer 402 may be less than 500 nanometers. The diffusion barrier layer 402 may additionally comprise a plasmon absorbing material at the interface between diffusion barrier layer 402 and Metal-I layer 404 as described above. It should be understood that the foregoing dimensions are exemplary, non-limiting values.

Figure 5:
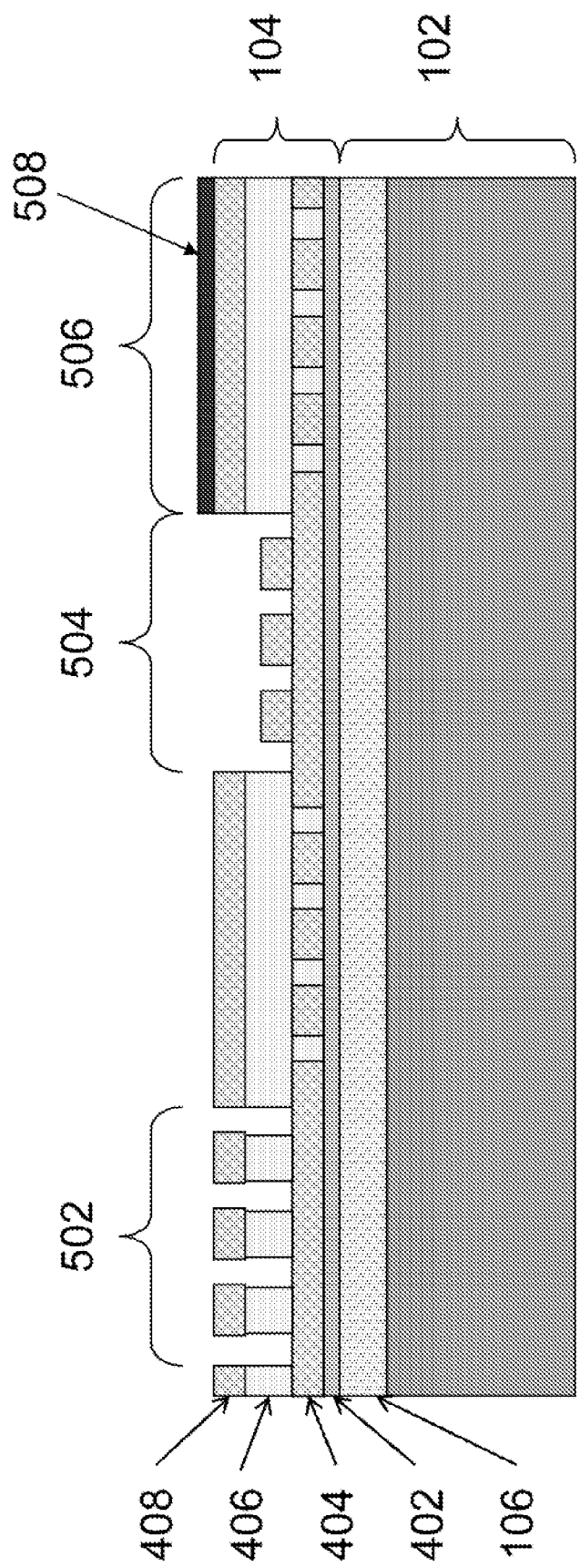
FIG. 5 illustrates features of exemplary alternative embodiments of a plasmonic backplane in accordance with the subject matter described herein.

In FIG. 5, features in common with the features illustrated in the aforementioned figures are shown with the same reference numbers and are not described again. FIG. 5 illustrates features of an exemplary alternative embodiment of a plasmonic backplane 104 in accordance with the subject matter described herein. It is understood that these features may be used in part or in any combination. An alternative design for a plasmonic scattering region 502 comprises plasmonic scattering features defined in both the metal-II layer 408 and the underlying dielectric interlayer 406, which may be formed by forming a chromium hardmask over metal-II layer 408 that contains a pattern corresponding to the plasmonic scattering features, etching through the metal-II layer and the dielectric interlayer using a directional etching process, and chemically removing the chromium hardmask. A second alternative design for a plasmonic scattering region 504 comprises plasmonic scattering features defined in metal-II layer 408 in contact with the metal-I layer 404. This structure may be formed by creating a pattern in dielectric interlayer 406 which exposes part or the entirety of the surface of metal-I layer 404 within the plasmonic scattering region using photolithography and chemical etching, depositing the metal-II layer by physical vapor deposition, forming a chromium hardmask over the resulting non-planarized metal-II layer 408 that contains a pattern corresponding to the plasmonic scattering features in plasmonic scattering region 504, and etching away part of the metal-II layer using a directional etching process to create plasmonic scattering features. For some applications, it may be advantageous to further encapsulate part or the entirety of the surface of metal-II within a plasmonic via region 506 using an encapsulation layer 508, which may be formed from oxide or nitride materials, or from organic materials or biological material. This process is used to form a plasmonic via region with encapsulation layer 506, which may be useful in later stages of fabrication for controlling the attachment sites for biological material.

Figure 6:
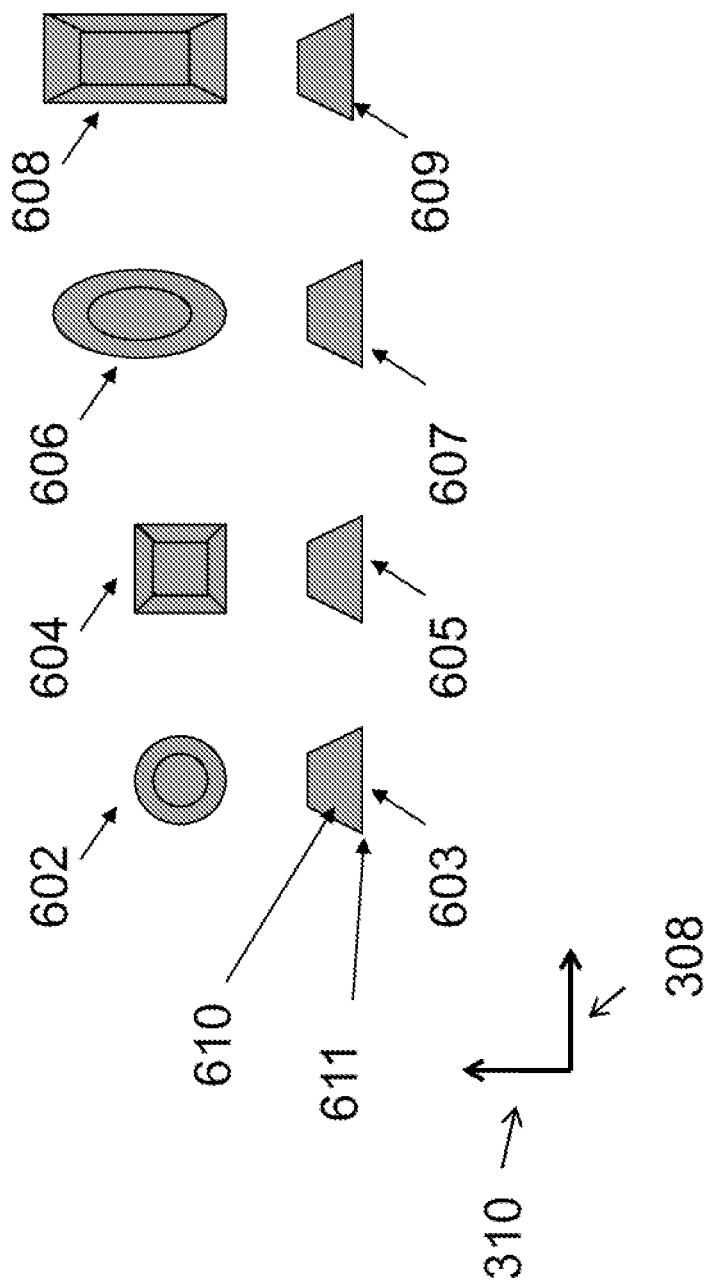
FIG. 6 illustrates exemplary geometries for plasmonic scattering features that may be arranged to construct plasmonic scattering regions and plasmonic via regions.

FIG. 6 illustrates exemplary geometries for plasmonic scattering features that may be arranged to construct plasmonic scattering regions and plasmonic via regions. These plasmonic scattering features can be formed using known deposition, lithography and etching techniques. An exemplary circular geometry is shown in cross section 603 and from the top 602. Feature sidewall angle 610 is preferably 90 degrees, but can vary from 10 degrees to 90 degrees depending on design and fabrication process. Feature contact angle to the underlying layer, 611, will be determined by the wetting properties of the materials used and the process conditions, but will preferably be 0 degrees. Adhesion layers known in the art, such as chromium or titanium thin films, may be used to change the contact angle. However, such films may reduce performance by causing additional propagation loss for guided plasmonic modes and surface plasmon polaritons. In another embodiment, the plasmonic scattering features may have a square geometry, shown in cross section 605 and from the top 604. In yet another embodiment the aforementioned geometries may be elongated in the x or y direction to form an ellipsoidal geometry, shown in cross section 607 and from the top 606, or a rectangular geometry, shown in cross section 609 and from the top 608. It should be understood that the circular, square, ellipsoidal and rectangular shapes described above and exemplary, non-limiting examples and that other shapes of the plasmonic scattering features include triangular, cylindrical, pyramidal, cross-shaped, trapezoidal, conical, annular and combinations thereof.

Exemplary lateral dimensions for plasmonic scattering features are in the range of 10 nanometers to 1 micrometer. Exemplary thicknesses for plasmonic scattering features are in the range of 10 nanometers to 500 nanometers. Preferably scattering feature volume is chosen to be large enough to provide strong scattering with high albedo and small enough to suppress higher order resonances.

Figure 7:
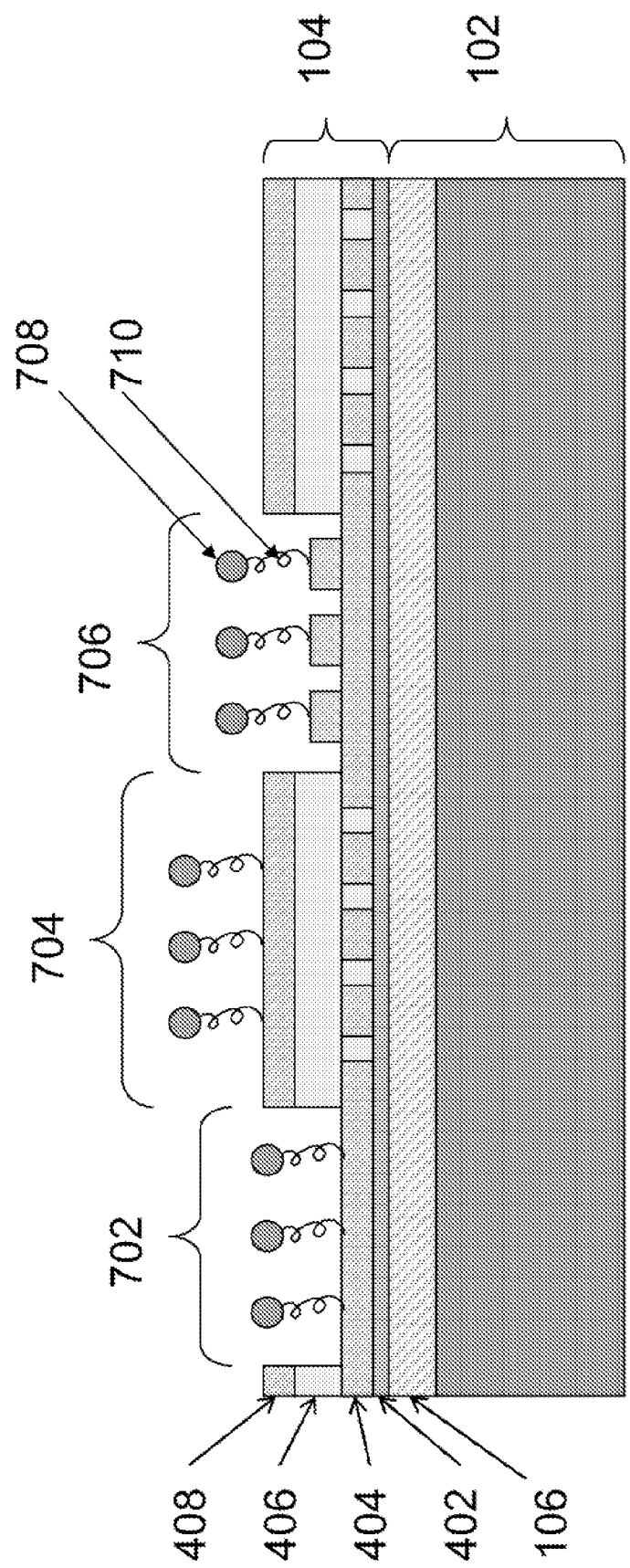
FIG. 7 illustrates an exemplary embodiment of a plasmonic backplane configuration in accordance with the subject matter described herein.

In FIG. 7, features in common with the features illustrated in the aforementioned figures are shown with the same reference numbers and are not described again. FIG. 7 illustrates an exemplary embodiment of a plasmonic backplane configuration in accordance with the subject matter described herein. In this embodiment, a plasmonic scattering region 706 may comprise one or more metallic nanoparticles 708 tethered to the surface of plasmonic scattering features by biomaterial tether constructs 710. In a second embodiment, plasmonic via region 704 may comprise one or more metallic nanoparticles tethered to the metal-II layer 408 by biomaterial tether constructs. In yet another embodiment, a plasmonic scattering region 702 in which the arrangement of plasmonic scattering features has been removed or omitted may comprise one or more metallic nanoparticles tethered to the metal-I layer 404 by biomaterial tether constructs. In these embodiments, the metallic nanoparticles 708 can be themselves considered as plasmonic scattering features. The metallic nanoparticles may be formed of gold, silver, copper, aluminum or alloys thereof, preferably gold, and may be spherical or ellipsoidal in shape or other shapes. Exemplary dimensions for the metallic nanoparticles are in the range of 10 nanometers to 200 nanometers. The metallic nanoparticles can be fabricated using synthetic chemistry methods known in the art, further functionalized by either solution or solid-phase chemistries known in the art, and then directed to assemble on the surface of the plasmonic backplane by specific covalent or noncovalent reactions to form the biomaterial tether constructs.

Figure 8:
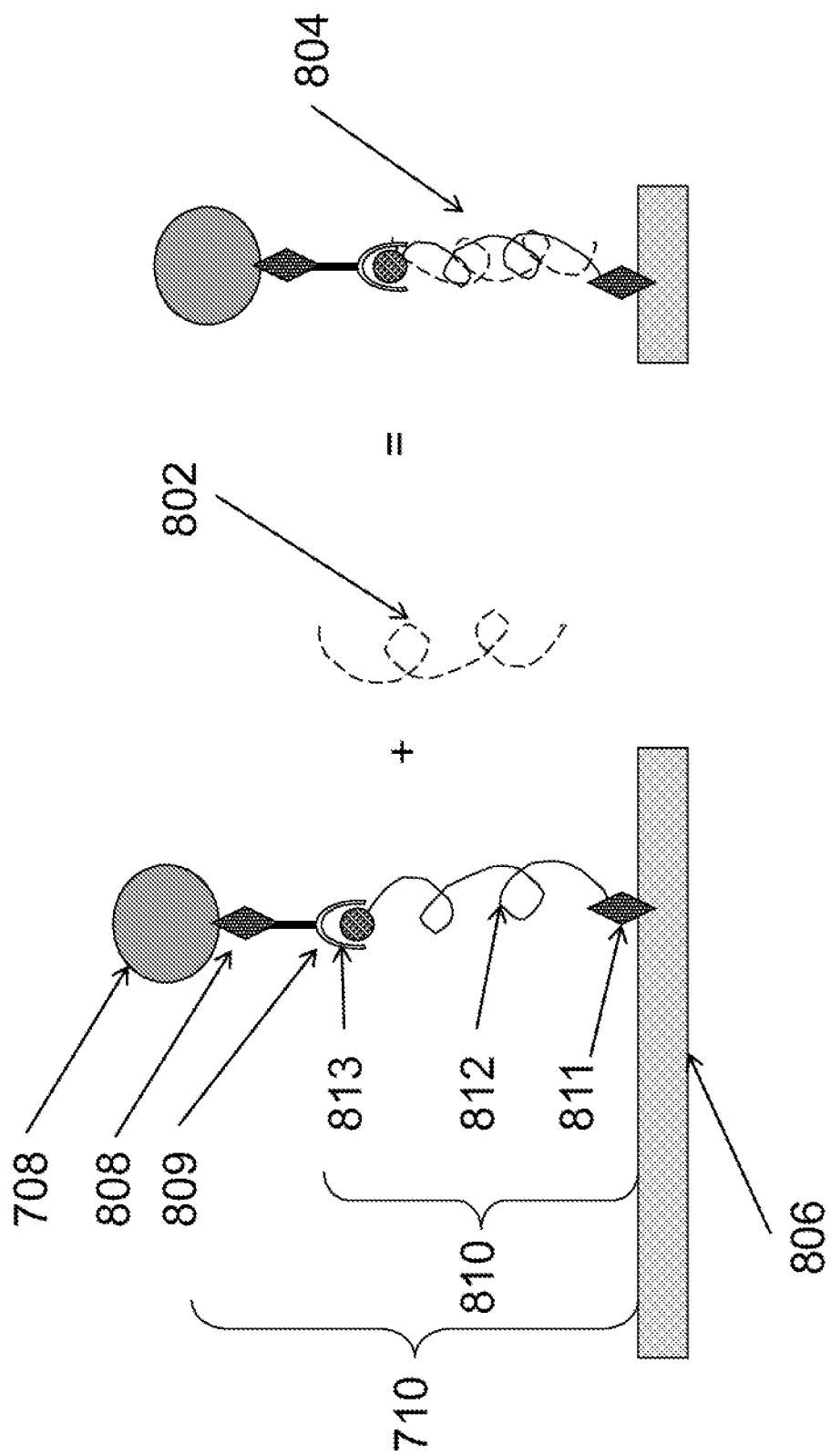
FIG. 8 illustrates an exemplary embodiment of a sensing modality according to the plasmonic backplane configuration of FIG. 7.

In FIG. 8, features in common with the features illustrated in the aforementioned figures are shown with the same reference numbers and are not described again. FIG. 8 illustrates an exemplary embodiment of a sensing modality according to the plasmonic backplane configuration of FIG. 7. Metallic nanoparticle 708 is conjugated with an adhesion linking construct 808, which may be an organic thiol compound, and a biotin binding construct 809, which may be streptavidin. Metallic surface 806, which may be a metal-I layer surface, plasmonic scattering feature, or metal-II layer surface, is conjugated with an oligonucleotide construct 810, comprising a second adhesion linking construct 811, which may be a thiol moiety, oligonucleotide 812, which may be single-stranded DNA, and a biotin moiety 813. Oligonucleotide construct 810 may be directed to react with the conjugated metallic nanoparticle to form biomaterial tether construct 710, according to the plasmonic backplane configuration depicted in FIG. 7. This configuration can be used to implement a oligonucleotide sensing modality for target oligonucleotide 802, which may be single-stranded DNA with sequence complementary to oligonucleotide 812. Sensing is achieved by the specific binding of oligonucleotide 812 to complementary oligonucleotide 802 to form hybridized oligonucleotide 804, which may comprise double-stranded DNA. The specific binding of oligonucleotide 812 to complementary oligonucleotide 802 results in a change in the mean separation distance between metallic surface 806 and metallic nanoparticle 708. Distance-dependent electromagnetic coupling between metallic surface 806 and metallic nanoparticle 708 results in a change in scattering efficiency that is detected as a change in the overall power transferred from the light source through the plasmonic backplane to the image sensor. This provides a first mechanism for detecting the presence of complementary oligonucleotide 802. In a further embodiment, complementary oligonucleotide 802 may be labeled with additional markers, such as fluorescent markers as are known in the art. In this case, the metallic nanoparticle 708 and the metallic surface 806 create an enhanced local field in the vicinity of the fluorescent marker, resulting in improved excitation efficiency when the system is illuminated at the excitation wavelength of the florescent marker. In this case, the de-excitation of the fluorescent marker is coupled to plasmonic mode excitations which aid in transferring power from the fluorescent marker through the plasmonic backplane to the image sensor. This provides a second mechanism for detecting the presence of complementary oligonucleotide 802, when it is labeled with one or more fluorescent markers.

Figure 9:
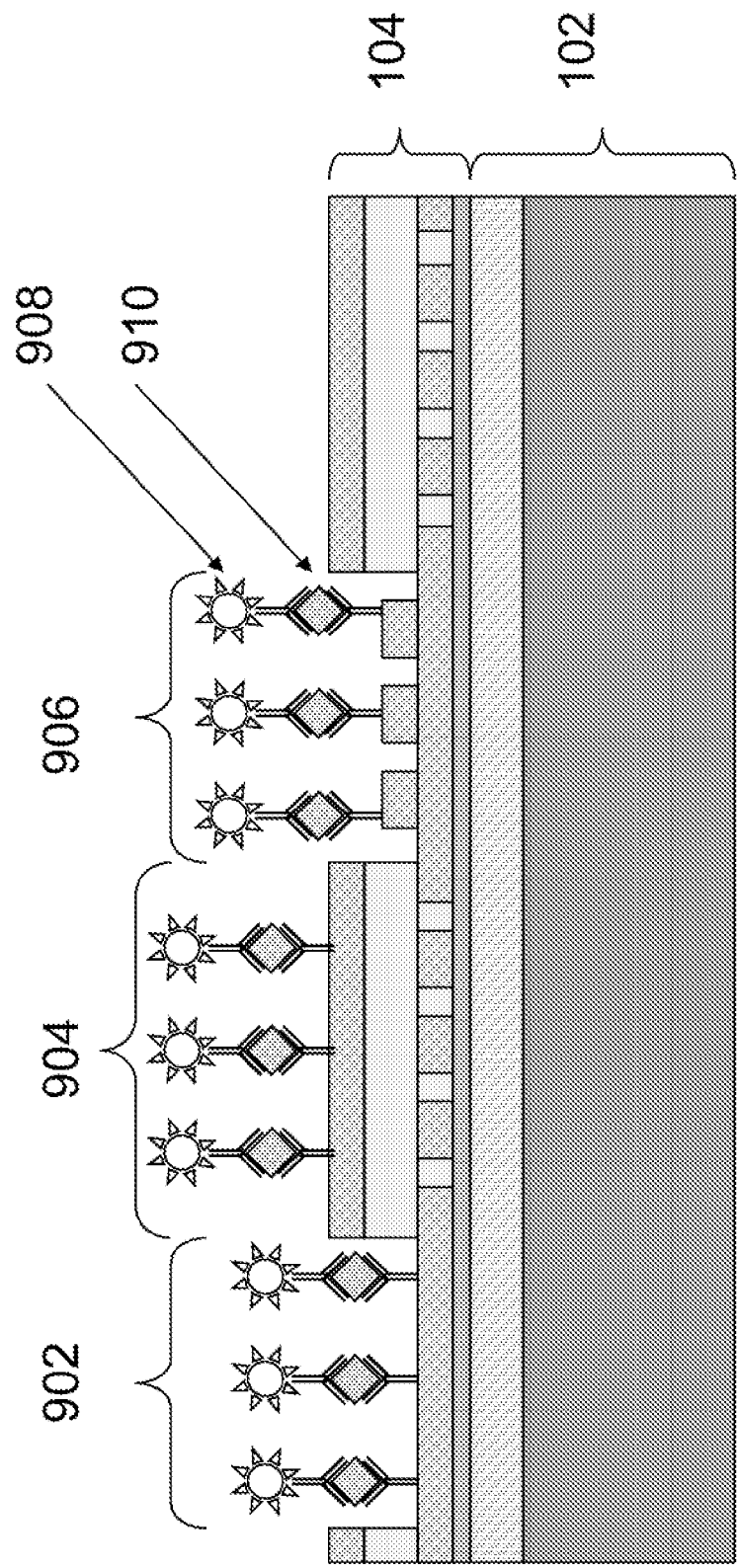
FIG. 9 illustrates a second exemplary embodiment of a plasmonic backplane configuration in accordance with the subject matter described herein.

In FIG. 9, features in common with the features illustrated in the aforementioned figures are shown with the same reference numbers and are not described again. FIG. 9 illustrates a second exemplary embodiment of a plasmonic backplane 104 configuration in accordance with the subject matter described herein. In this embodiment, a plasmonic scattering region 906 comprises one or more luminescence catalysts 908 tethered to the surface of plasmonic scattering features by sandwich assay constructs 910. In a second embodiment, plasmonic via region 904 comprises one or more luminescence catalysts tethered to the metal-II layer by sandwich assay constructs. In yet another embodiment, a plasmonic scattering region 902 in which the arrangement of plasmonic scattering features has been removed or omitted comprises one or more luminescence catalysts tethered to the metal-I layer by sandwich assay constructs. The luminescence catalyst may comprise an enzymatic bioluminescence system, such as a luciferase system, a fluorescence system, such as a quantum dot system (e.g., CdSe quantum dots), an organic fluorophore system (e.g., fluorescein), a fluorescent protein system (e.g., green fluorescent protein (GFP)), or a chemiluminescence system, such as a horseradish peroxidase system. The design of the plasmonic backplane can be customized for operation at the excitation and/or de-excitation frequency of the luminescence catalyst system used. For example, the dimensions and arrangement of the plasmonic scattering features can be selected to transfer power efficiently through the plasmonic backplane at the de-excitation frequency of the luminescence catalyst system while rejecting power at the excitation frequency.

Figure 10:
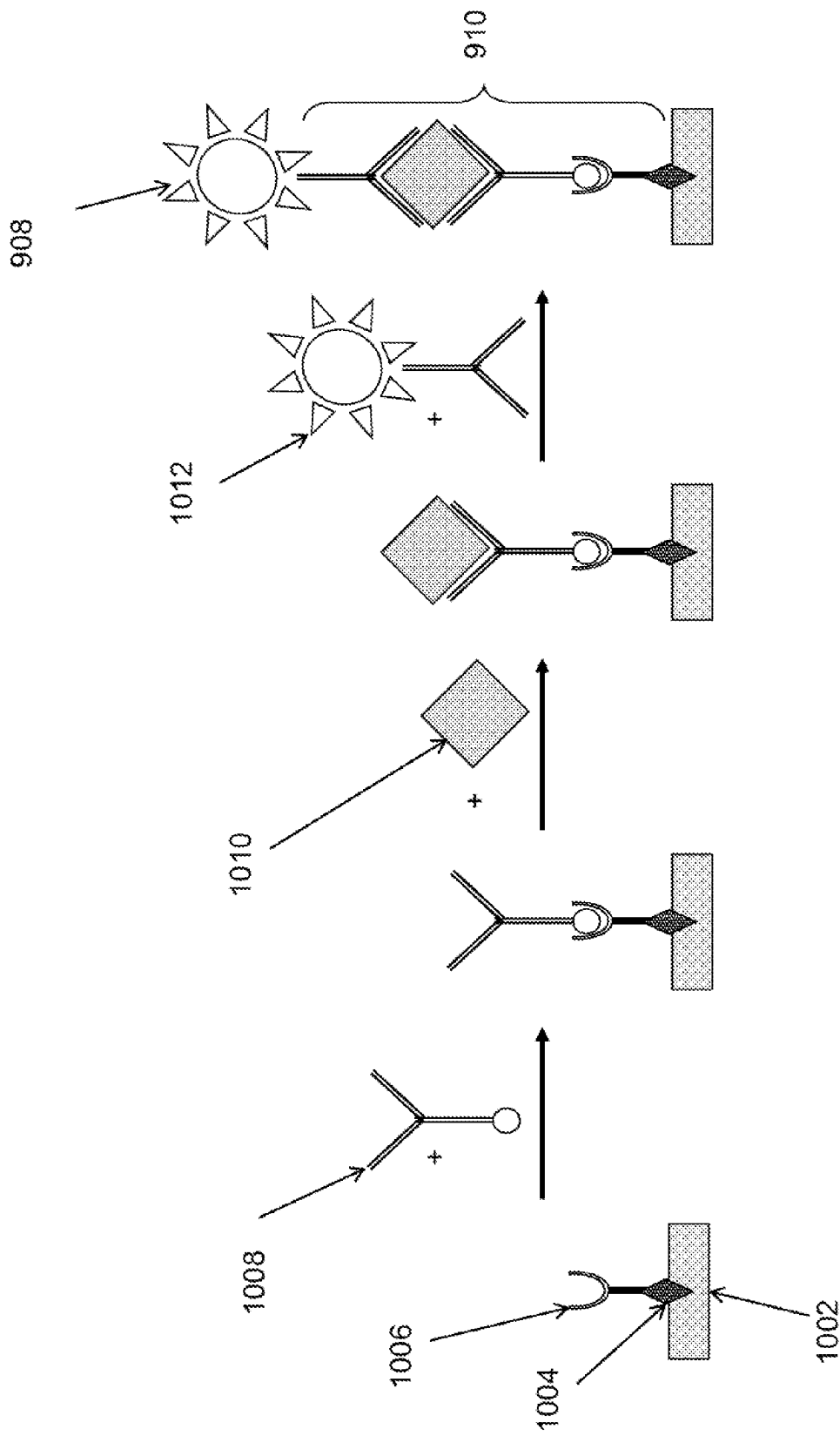
FIG. 10 illustrates an exemplary embodiment of a sensing modality according to the plasmonic backplane configuration of FIG. 9.

FIG. 10 illustrates an exemplary embodiment of a sensing modality according to the plasmonic backplane configuration of FIG. 9. Metallic surface 1002, which may be a metal-I layer surface, plasmonic scattering feature, or metal-II layer surface, is conjugated with an adhesion linking construct 1004, which may be a thiol moiety, and a biotin binding construct 1006, which may be streptavidin. Sequential reaction with a biotinylated primary antibody 1008, target antigen 1010, and luminescence catalyst conjugated secondary antibody 1012 forms sandwich assay construct 910, which tethers luminescence catalyst 908 in the vicinity of the plasmonic backplane, such that near-field interactions can preferentially result in the luminescence catalyst creating surface plasmon polaritons and guided plasmonic modes upon de-excitation. Power transfer from incident light to surface plasmon polaritons and guided plasmonic modes provides a mechanism for detecting the presence of target antigen 1010, e.g. the guided plasmonic modes are coupled to the image sensor which produces a signal responsive to the received coupled plasmonic modes.

In FIG. 11a-i the features in common with the features illustrated in the aforementioned figures are shown with the same reference numbers and are not described again. FIGS. 11a-i illustrate a method of manufacturing an integrated plasmonic sensing device in accordance with a second aspect of the subject matter described herein. The plasmonic backplane shown in this embodiment comprises one or more plasmonic scattering regions and one or more plasmonic via regions, in which guided plasmonic modes form intermediate channels that transfer power to an underlying monolithically integrated image sensor comprising one or more image sensor pixels.

Figure 11A:
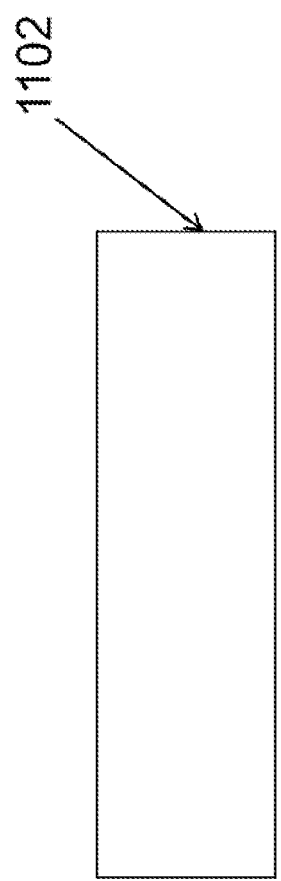
Figure 11B:
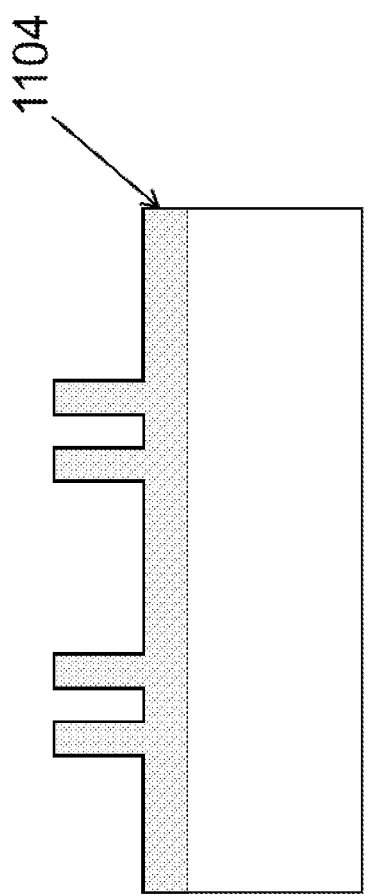
Figure 11E:
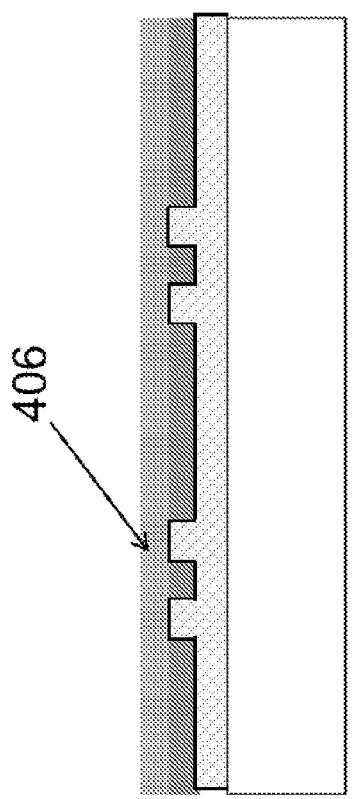
Figure 11F:
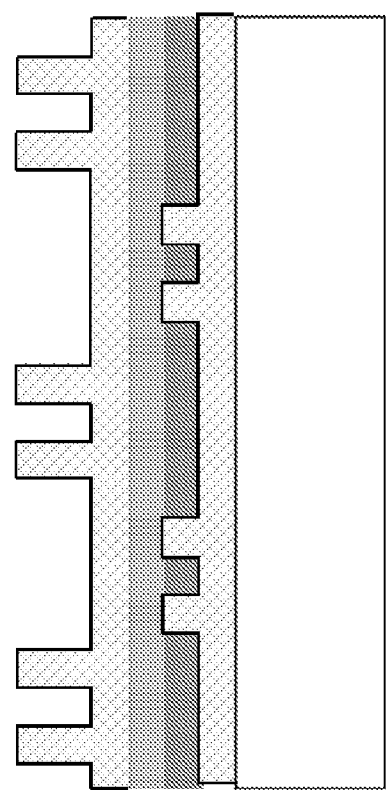
Figure 11G:
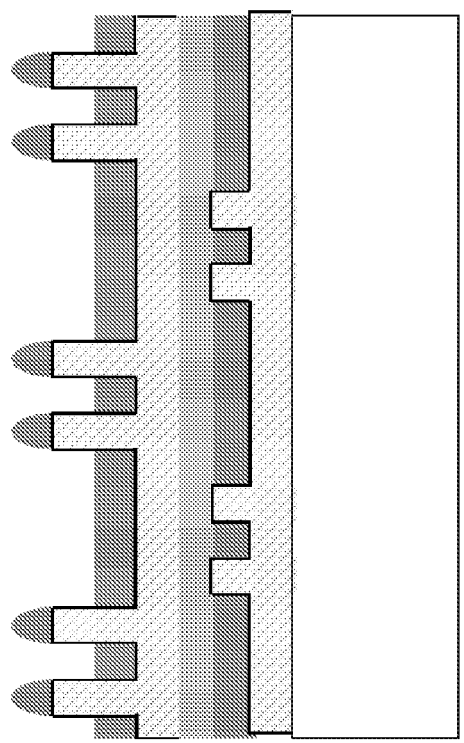
Figure 11H:
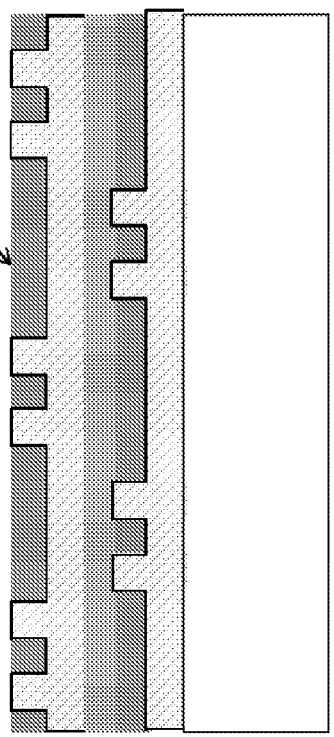
Figure 11I:
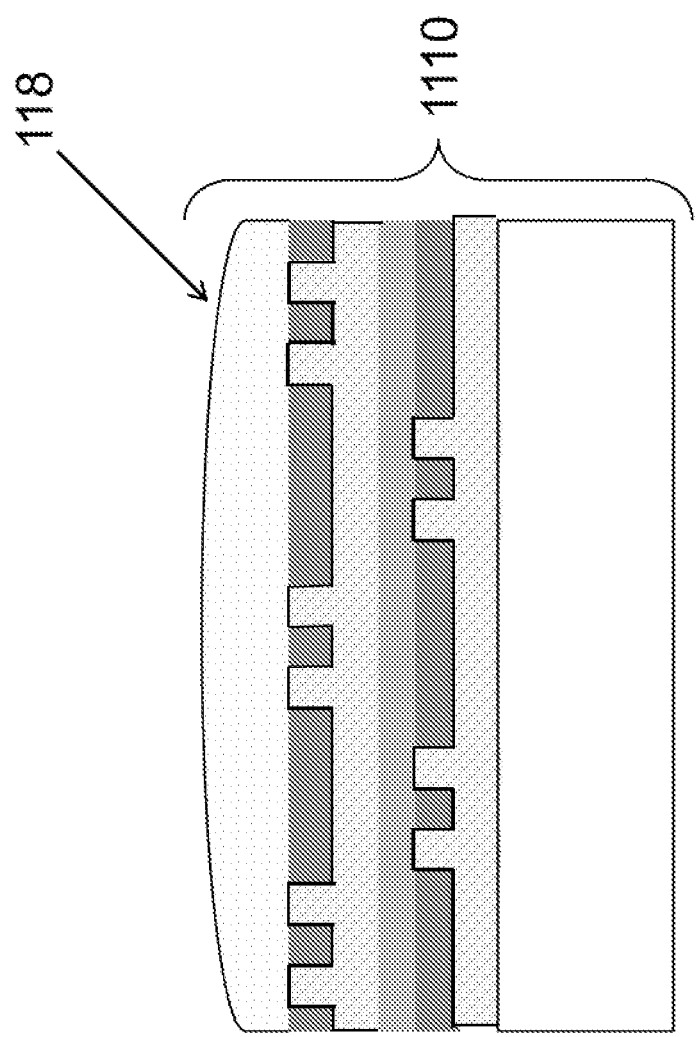

A substrate comprising one or more image sensors 1102 is first chemically treated to remove any particles or residues from its surface. (FIG. 11a) Such chemical treatment may include exposure to an oxygen plasma and/or mechanical abrasion and/or sonication in a bath of organic solvent to remove the textured microlens layer commonly formed on image sensors to enhance the light collection. Removing the microlens layer provides a substantially flat surface for the fabrication of a plasmonic backplane. A layer of silica sol-gel is then formed and imprinted with a stamp to produce patterned silica template layer 1104 comprising structures that will define the plasmonic scattering features of the plasmonic via regions and components of the plasmonic scattering regions. These regions may be arranged in rows and columns as illustrated in FIG. 3. (FIG. 11b) A first metal layer 1106 such as a gold layer is then formed by physical vapor deposition over pattern 1104. (FIG. 11c) A chemical mechanical polishing (CMP) process is then used to planarize the surface of the chip, forming metal-I layer 404. (FIG. 11d) Together FIG. 11b, FIG. 11c, and FIG. 11d depict a "gold damascene" process by analogy to the copper damascene process well known in the art of semiconductor integrated circuit manufacturing. Dielectric interlayer 406 is then formed, for example by physical vapor deposition over metal-I layer 404 and remaining silica template layer 1104. FIG. 11f, FIG. 11g, and FIG. 11h depict the formation of metal-II layer 408 by a gold damascene process as previously described. To functionalize the plasmonic backplane according to the configuration depicted in FIG. 7 (biotether) or FIG. 9 (conjugation with adhesion linking constructs), biological material 118, which comprises molecules tethered covalently or non-covalently to metal-II layer 408 and may additionally comprise aqueous buffer solutions used to control pH, such as phosphate-buffered saline (PBS), mixtures of solvents used to aid in dissolution such as dimethylsulfoxide, alcohols, or detergents (i.e., SDS, Tween-20), and other untethered organic molecules such as glucose, is formed on top the plasmonic backplane by one of the available techniques such as robotic spotting, inkjet printing or photolithography. (FIG. 11i) The processed substrate comprising one or more integrated plasmonic sensing devices 1110 is then diced into individual integrated plasmonic sensing devices which can be wire bonded into packages for electrical readout of the monolithically integrated image sensors, which may be ceramic leadless chip carrier (CLCC) packages. Alternatively, biological material 118 may be applied after the individual image sensor chips are packaged.

Figure 12:
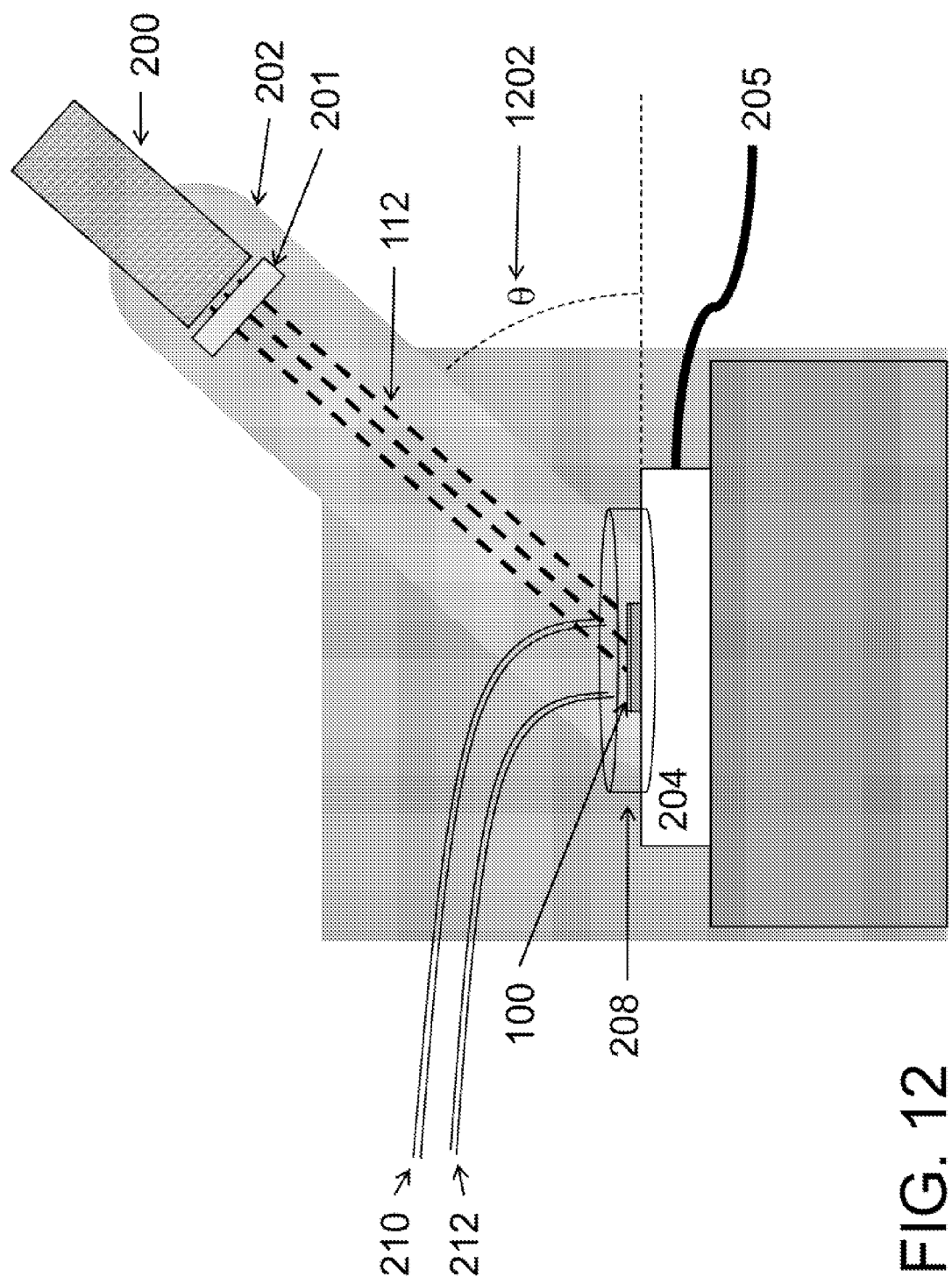
FIG. 12 illustrates a method for testing a biological substance in accordance with a third aspect of the subject matter described herein, comprising a method of testing a biological substance according to the sensing modality of FIG. 8.

In FIG. 12 the features in common with the features illustrated in the aforementioned figures are shown with the same reference numbers and are not described again. FIG. 12 illustrates a method for testing a biological substance in accordance with a third aspect of the subject matter described herein, comprising a method of testing a biological substance according to the sensing modality of FIG. 8. An integrated plasmonic sensing device 100 is placed in the sensor headboard 204 of the apparatus depicted in FIG. 2. A sample that may contain complementary oligonucleotide target molecules is provided in a buffer solution through fluid input 210 and flows over the surface of the integrated plasmonic sensing device 100 in flow cell 208 towards fluid return 212, where effluent is collected as waste. The power received by the image sensor is monitored over interface cable 205 while the illumination conditions are modified. The angle of incidence 1202 is modified by rotating illumination arm 202, preferably in a sinusoidal pattern. Simultaneously, polarization filter 201 rotates to change the polarization angle of the incident light 112. Light source 200 can comprise a supercontinuum fiber laser with an acousto-optic tunable filter (AOTF), allowing the color of the incident light to be varied in time. Each image sensor pixel is monitored during the measurement period and a software algorithm is used to track and interpolate the maximum power illumination condition for each plasmonic scattering region. The incident light can be modulated at a certain frequency and this frequency can then be filtered out from the image sensor signals in order to improve signal to noise ratio.

Additionally, signal can be combined from one or more image sensor pixels, preferably using robust statistical techniques such as median filtering and incorporating an areal weighting function. For arrangements of plasmonic scattering features that cause a plasmonic scattering region to couple light to guided plasmonic modes according to the incident light polarization angle, the polarization angle of the incident light can be modulated at a certain frequency and this frequency can then be filtered out from the combined image sensor signals in order to further improve signal to noise ratio. For example, an arrangement of plasmonic scattering features on a square grid may preferentially launch guided plasmon modes in the x direction for a first angle of polarization and in the y direction for an orthogonal angle of polarization. In a second example, an arrangement of plasmonic scattering features on a hexagonal grid may preferentially launch guided plasmon modes in three principle directions for three corresponding angles of polarization.

Figure 13:
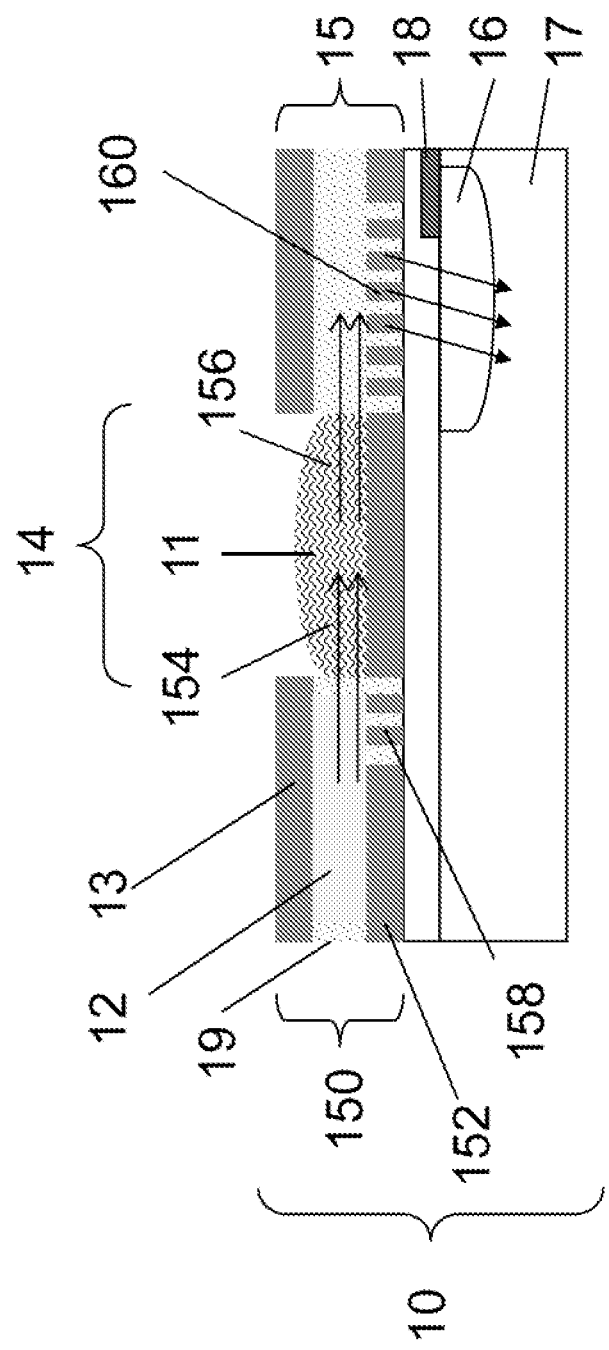
FIG. 13 illustrates a cross-section of a first embodiment of a sensor in accordance with the subject matter described herein utilizing an plasmonic source, an interaction region, and a photodetector monolithically integrated on a semiconductor substrate.

Turning to FIG. 13, there is shown a cross-section of a first embodiment of a sensor 10 utilizing a plasmonic source 150 and a photodetector 16 monolithically integrated on a semiconductor substrate 17. The following description proceeds with reference to a biochip embodiment; however, this aspect of the described subject matter is not limited to use with biological materials. The sensors of the described embodiments can be used to test non-biological materials in solid and fluid form. Incident plasmonic mode excitations 154 are emitted by plasmonic source 150 comprising an organic semiconductor p-n bi-layer 12, bottom electrode 152, and top electrode 13. The top and bottom electrodes can be made of gold or alternatively the top electrode can be made of a bi-layer of silver and gold and/or the bottom electrode can be made of a bi-layer of gold and silver to reduce absorption and improve performance. These incident plasmonic mode excitations interact with biological substance under test 11 in interaction region 14. The biological substance under test 11 can be disposed in the form of a gel or liquid. When the biological substance under test includes fluorescent markers, the luminescence excited in the biological substance under test by the incident plasmonic mode excitations is coupled to secondary plasmonic mode excitations 156 which then couple via a plasmonic mode scattering region 15 to a photodetector 16. The plasmonic mode scattering region may comprise an arrangement of one or more resonant plasmonic scattering features 160. The plasmonic mode scattering region is designed to couple plasmonic mode excitations at the wavelength of luminescence as opposed to the wavelength of excitation and can be optimized using conventional electromagnetic simulation software. A plasmonic mode filtering region 158 may also be formed in the bottom electrode 152 to improve performance by partially reflecting the secondary plasmonic mode excitations resulting from luminescence, comprising an arrangement of one or more resonant plasmonic scattering features 160. In a further embodiment, the rejection of the incident plasmonic mode excitations relative to the secondary plasmonic mode excitations resulting from luminescence can be further enhanced by a thin film interference filter (not shown in FIG. 13) that can be formed on the surface of the photodetector 16.

When the biological substance under test includes absorption markers, the incident plasmonic mode excitations interact with the absorption markers attached to target molecules that are bound through covalent or non-covalent interactions in the vicinity of the interaction region, which results in a reduction in the intensity of plasmonic mode excitations that are transmitted through the interaction region. The reduction in the intensity of the transmitted plasmonic mode excitations is proportional to the amount of target molecules in the vicinity of the interaction region. The reduced intensity plasmonic mode excitations are coupled via a plasmonic mode scattering region to a photodetector as described in the previous paragraph.

When the biological substance under test is marker-free, the status of a molecular recognition event at an interaction region can be derived from a change in refractive index in the interaction region that results from the molecular recognition event. The change in refractive index in the interaction region resulting from the molecular recognition event results in a reduction or enhancement in the intensity of plasmonic mode excitations that are transmitted through the interaction region, due to modified constructive or deconstructive interference of multiply-reflected plasmonic mode excitations in the cavity defined by the limits of the interaction region. The reduction or enhancement in the intensity of the transmitted plasmonic mode excitations is proportional to the amount of target molecules in the vicinity of the interaction region. The reduced or enhanced intensity plasmonic mode excitations are coupled via a plasmonic mode scattering region 15 to a photodetector 16 as previously described.

An exemplary width of the plasmonic source 150 is between 100 nanometers and 10 microns, an exemplary width of the interaction region is between 100 nanometers and 10 microns, and an exemplary width of plasmonic mode scattering region 15 is typically between 100 nanometers and 10 microns. An exemplary width of the plasmonic mode filtering region 158 is between 50 nanometers and 5 microns and an exemplary thickness of the top and bottom electrodes 13 and 152 is in the range of 10 nanometers to 1 micron. An exemplary thickness of the semiconductor bi-layer 12 is between 50 nanometers and 300 nanometers. It should be understood that the dimensions just described are non-limiting examples and that dimensions falling outside the described ranges can be used.

Semiconductor substrate 17 can be made of silicon and the photodetector 16 can be implemented using known processing techniques in photodiode, complementary metal oxide semiconductor (CMOS) sensor, or charge coupled device (CCD) configurations as described for example in the article by M. L Adams et al., "Microfluidic integration on detector arrays for absorption and fluorescence micro-spectrometers" Sensor and Actuators, Vol. A104, 2003, pp. 25-31. As illustrated in FIG. 13, the photodetector 16 can be located such that it is not aligned with interaction region 14. For example, in FIG. 13, photodetector 16 is not under the interaction region 14, but rather is offset laterally from interaction region 14. The plasmonic source 150 can be implemented as an organic light emitting diode utilizing known processing techniques as described for example in the article by D. M. Koller, et al., "Organic plasmon emitting diode" Nature Photonics 2, 684 (2008). A dielectric layer 19 can be used to encapsulate the plasmonic source 150 and the plasmonic mode scattering region 15 over the photodetector area. Dielectric layer 19 can be made using a spin-on silica sol-gel or alumina layers deposited using atomic layer deposition. The interaction region 14 can be formed during the fabrication of the top electrode 13. The semiconductor p-n bi-layer 12 is operated by applying voltage between electrodes 152 and 13 to create plasmonic mode excitations using the plasmonic source comprising bi-layer 12 and electrodes 152 and 13. The photodetector is operated by applying voltage between electrode 18 and the substrate 17.

Figure 14:
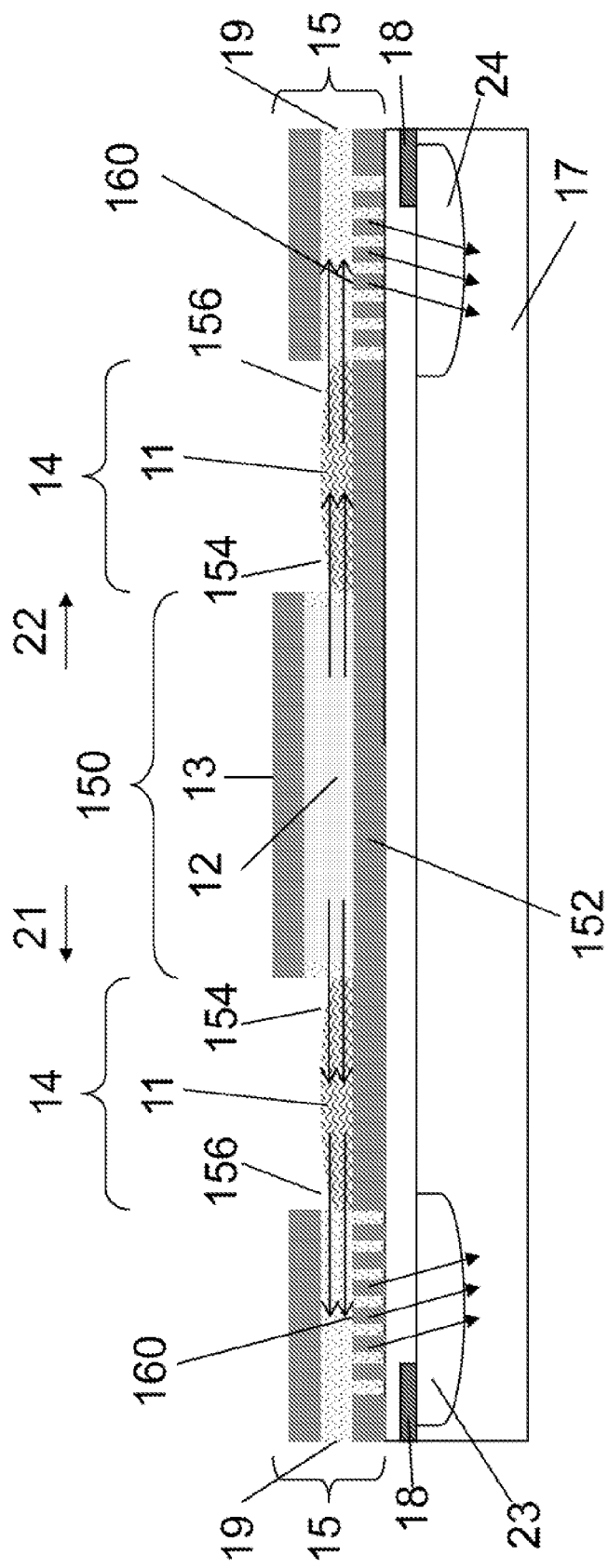
FIG. 14 illustrates a cross-section of a second embodiment of a sensor in accordance with the subject matter described herein which is based on the first embodiment but utilizes a bi-directional plasmonic source.

In FIG. 14 the features in common with the features of the biochip illustrated in FIG. 13 are shown with the same reference numbers and are not described again. In FIG. 14, the same concept as described above in relation to FIG. 13 is extended to provide for plasmonic mode excitations 154 emitted from the plasmonic source 150 to be directed in both directions 21, 22 and received by two photodetectors 23 and 24 after passing through two interaction regions. Here the plasmonic mode filtering region is omitted. This structure, in addition to better utilizing the plasmonic mode excitations emitted by a single plasmonic source, is also better suited for implementation of an interdigital structure described in relation to FIG. 15.

Figure 15:
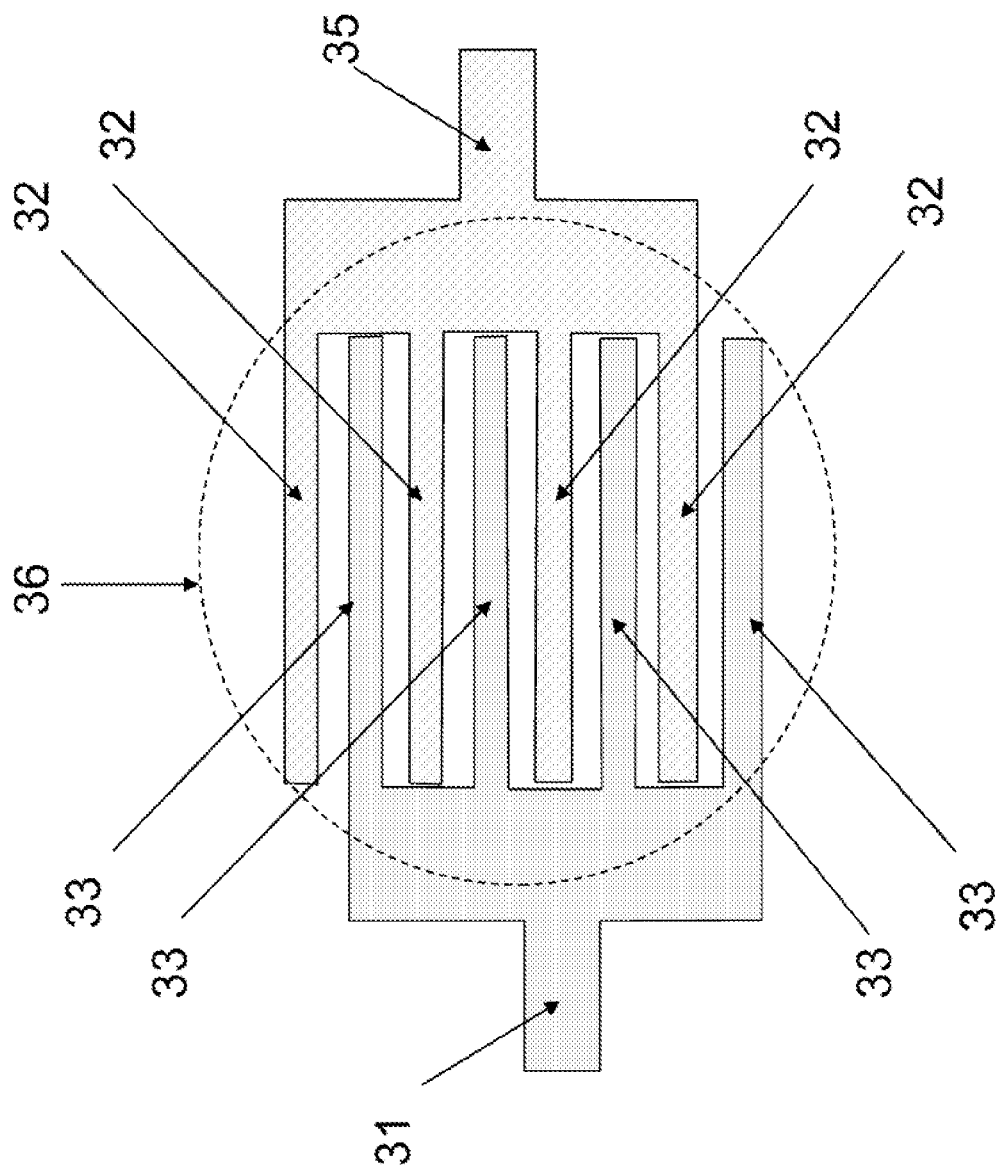
FIG. 15 illustrates a top view of the sensor of FIG. 2, which utilizes an interdigital configuration of the plasmonic sources and photodetectors.

FIG. 15 shows an interdigital configuration of plasmonic sources 33 and photodetectors 32. As shown in FIG. 15 the electrodes 31 and 35 associated with plasmonic sources 33 and photodetectors 32 within a single measurement region 36 are made in the form of interdigital combs, each comb connected to the same driving electrodes 31, 35 extending to the periphery of the biochip.

Figure 16:
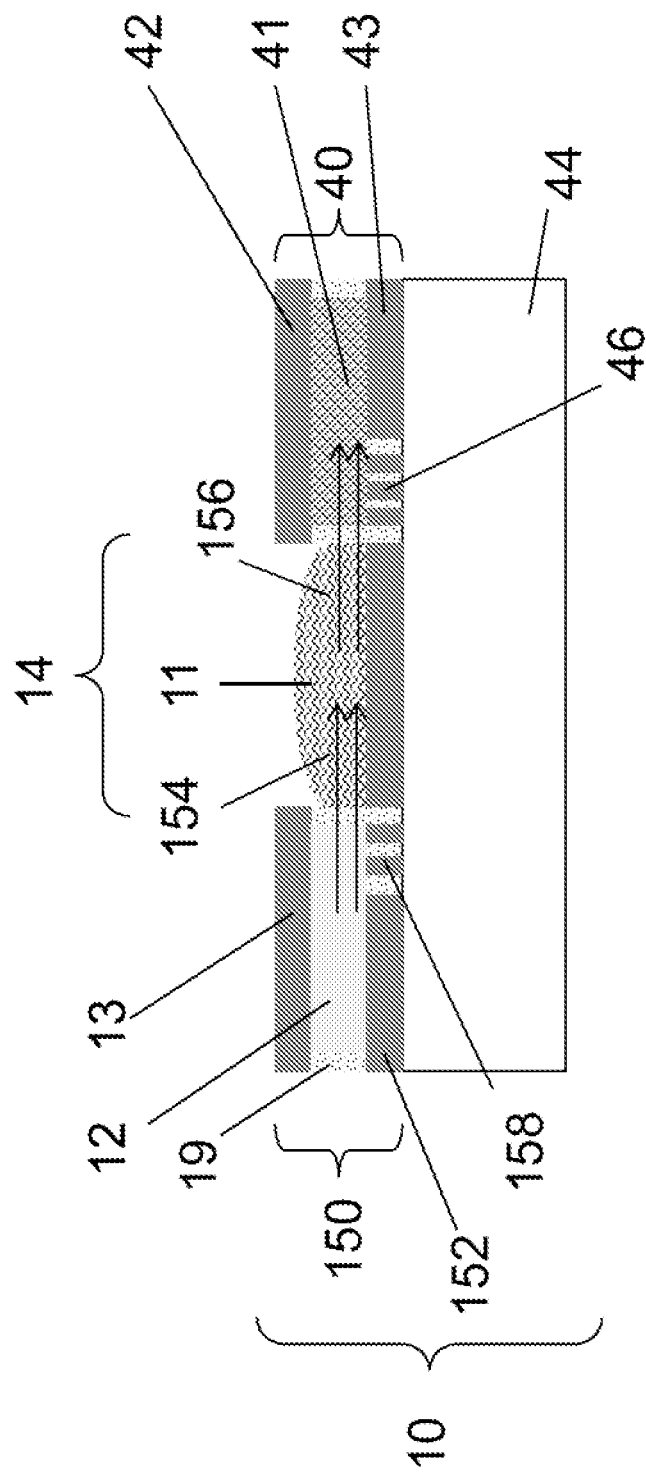
FIG. 16 illustrates a cross-section of third embodiment of a sensor in accordance with the subject matter described herein utilizing a plasmonic source and a thin-film photodetector.

In FIG. 16, the features in common with the features of the biochip illustrated in FIG. 13 are shown with the same reference numbers and are not described again. FIG. 16 shows a cross-section of a biochip 10 similar to that described in relation to FIG. 13 but where the photodetector 40 is realized in a thin-film form as opposed to being made in a semiconductor substrate. Such a photodetector 40 includes a semiconductor p-n bi-layer 41, bottom electrode 43, and top electrode 42 and could be realized in a semiconductor polymer material as described in the article by K. S. Narayan et al., "Novel strategies for polymer based light sensors" Thin Solid Films Vol. 417, 2002, pp. 75-77. The photodetector semiconductor bi-layer 41 can be formed separately from the plasmonic source semiconductor bi-layer 12. Alternatively, due to source/detector reciprocity, the photodetector 40 could be fabricated in the same semiconductor polymer layer as the plasmonic source 150. In this latter case the plasmonic source and detector areas can be simply formed by the photolithographic definition of the top and bottom electrodes. The advantage of this alternative is a significantly simplified fabrication procedure and the corresponding reduction in biochip manufacturing costs. For example, low cost glass or ceramic substrate 44 can be used. To overcome potential electrical cross talk problems and to improve performance, an incident plasmonic mode excitation filtering region 158 and a secondary plasmonic mode excitation filtering region 46, as shown in FIG. 16, can be used.

Figure 17:
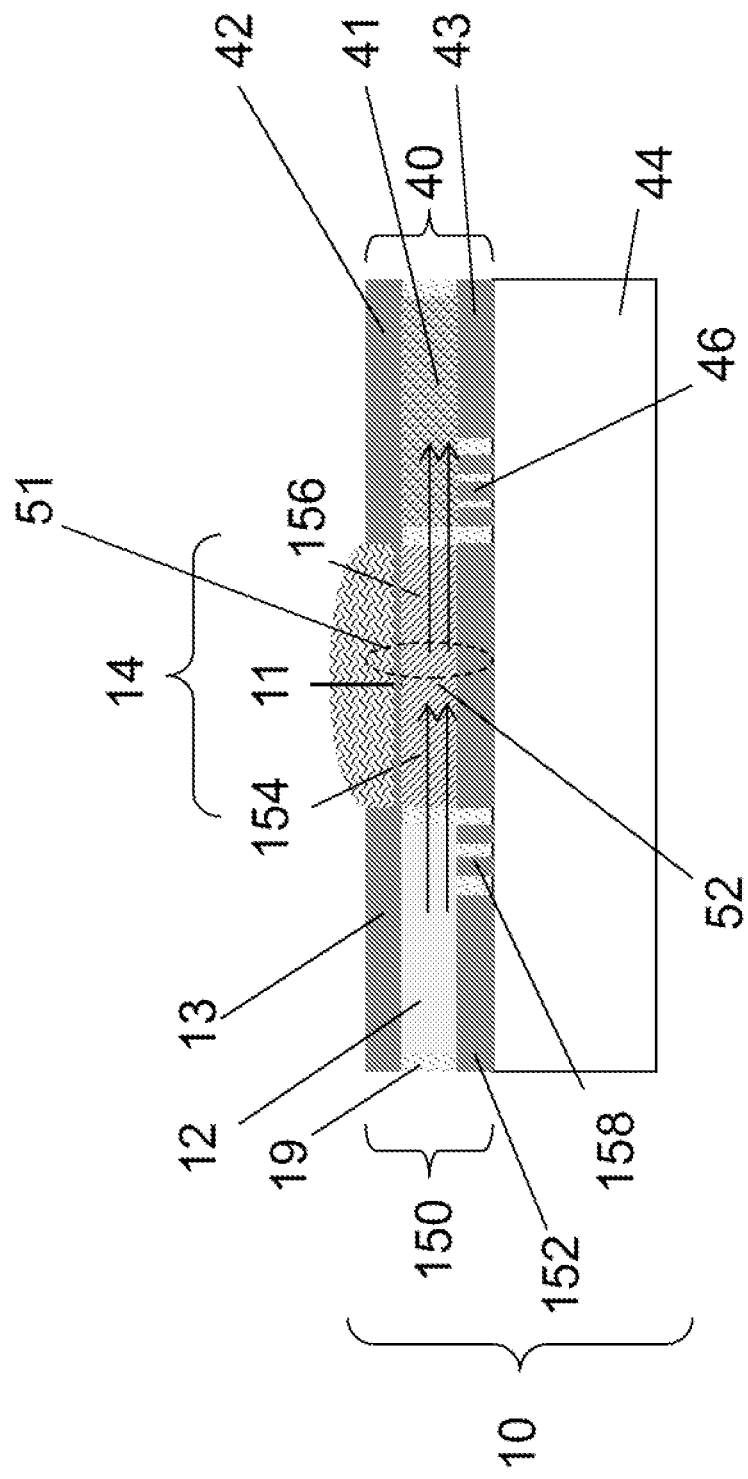
FIG. 17 illustrates a cross-section of fourth embodiment of a sensor in accordance with the subject matter described herein utilizing a plasmonic source and a thin-film photodetector, in which the plasmonic mode excitation region comprises a four layer metal-dielectric-metal-dielectric plasmonic waveguide.

In FIG. 17, the features in common with the features of the biochip illustrated in FIG. 16 are shown with the same reference numbers and are not described again. FIG. 17 shows a cross-section of a biochip similar to that described in relation to FIG. 16 but where the interaction region 14 comprises a four layer metal-dielectric-metal-dielectric plasmonic waveguide 51, in which plasmonic mode excitations are confined to propagate on an arrangement of three metal-dielectric interfaces: biological substance under test 11 and metal corresponding to top electrodes 13 or 42 (which may preferably be thinned in interaction region 14), metal corresponding to top electrodes 13 or 42 and dielectric core layer 52, and dielectric core layer 52 and metal corresponding to bottom electrodes 152 or 43. This geometry may provide superior encapsulation of the semiconductor bi-layers used to form the plasmonic source and the thin-film photodetector. Dielectric core layer 52 may be formed of silica sol-gel. Alternatively, the dielectric core layer may be fabricated in the same semiconductor polymer layer as the plasmonic source and/or the same semiconductor polymer layer as the thin-film photodetector. The advantage of this alternative is a significantly simplified fabrication procedure and the corresponding reduction in biochip manufacturing costs. A disadvantage of this alternative is an increased absorption of energy from plasmonic mode excitations in the dielectric core layer 52.

In the previously described embodiments, control of the wavelength emitted by the plasmonic source can be achieved by an appropriate choice of p-n bi-layer material. Additional selection of the wavelengths of plasmonic mode excitations that couple to the interaction region can result from an appropriately designed incident plasmonic mode excitation filtering region. In the case when the biological substance under test is marked with fluorescent markers the plasmonic source and the incident plasmonic mode excitation filtering region are tuned to transmit plasmonic mode excitations at the wavelength of excitation of the fluorescent markers and the photodetector and secondary plasmonic mode excitation filtering region are tuned for the wavelength of emission of the fluorescent markers. In the instance where more than one fluorescent marker is used at one measurement region, the corresponding number of the plasmonic sources and photodetectors can be associated with the one measurement region and each additional source/detector pair can be tuned to the excitation/emission wavelength of each additional fluorescent marker used at this measurement region.

Figure 18:
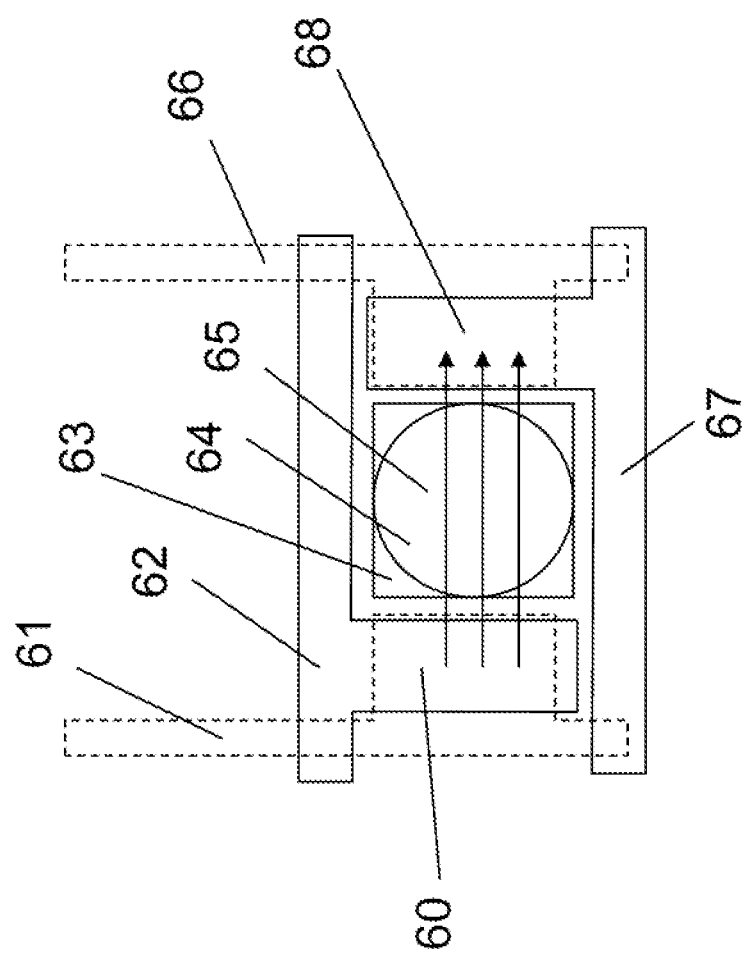
FIG. 18 illustrates a top view of a general embodiment of a sensor in accordance with the subject matter described herein utilizing electromagnetic field excitation or interaction.

FIG. 18 illustrates a top view of a plasmonic source 60/photodetector 68 pair connected by an interaction region 63 and associated with each measurement region 64 of the plurality of measurement regions. The pair includes bottom 61 and top 62 electrodes of the plasmonic source 60, a interaction region 63 (as described above), a measurement region 64 formed on the surface of the interaction region, and a thin film photodetector 68 comprising a top electrode 67 and bottom electrode 66. The plasmonic mode excitations emitted by the plasmonic source 60 are coupled into the interaction region where the field of the plasmonic mode excitations interacts with the biological substance 65 over the measurement region 64 and is then coupled from the interaction region to the thin film photodetector 68.

Figure 18A:
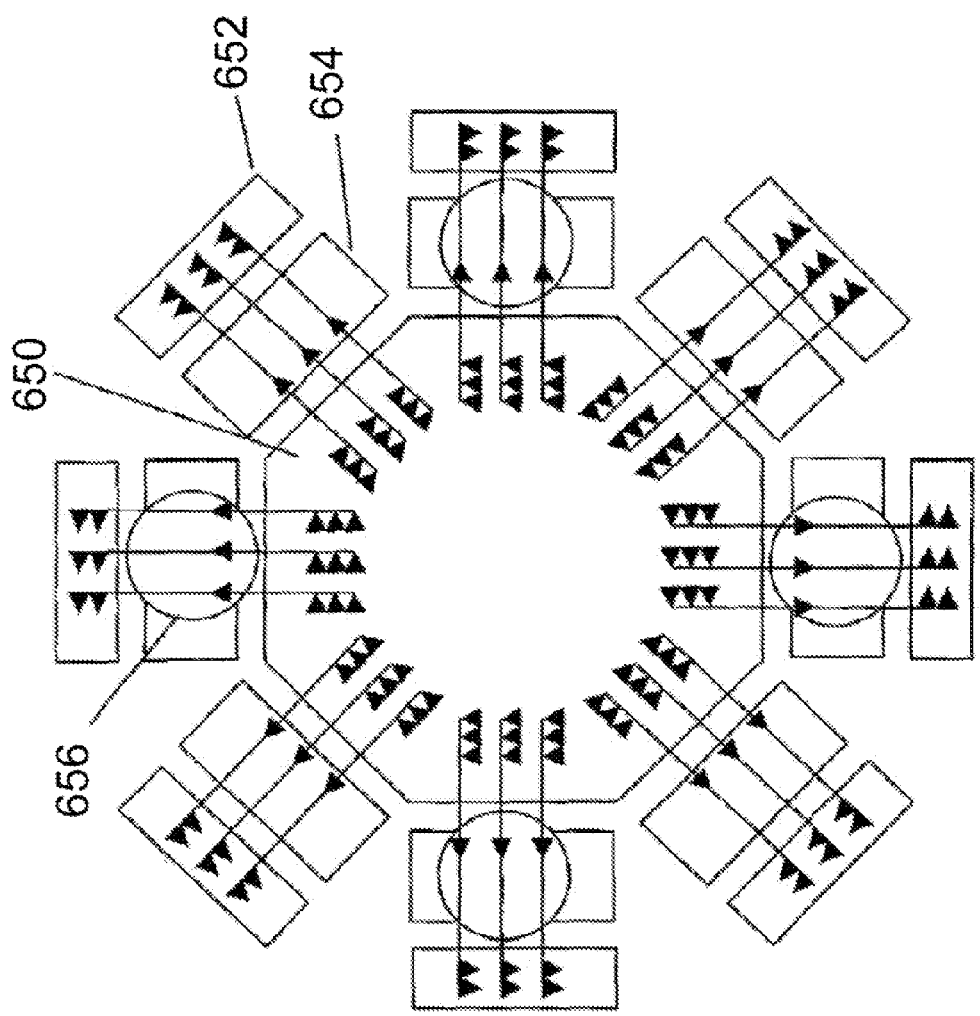
FIG. 18A illustrates a top view of another embodiment of a sensor in accordance with the subject matter described herein utilizing electromagnetic field excitation or interaction and a plasmonic source sharing scheme with reference paths.

FIG. 18A illustrates a top view of another alternative of a plasmonic source/photodetector arrangement where one plasmonic source 650 is shared between 8 interaction region 654/photodetector 652 pairs. This arrangement contains 4 measurement regions 656 formed on top of four out of eight interaction regions whereas four remaining interaction regions act as reference paths. These reference paths enable separation of luminescence, absorbance, or refractive index changes associated with binding events at each of the measurement regions and luminescence, absorbance, or refractive index changes due to temperature changes during molecular recognition. Such reference paths allow for continuous monitoring of molecular recognition at different sites as the temperature of the chip is ramped up or down and enables the determination of measurement regions with non-specifically bound molecules which tend to decouple above certain characteristic temperatures whereas specifically bound molecules remain bound above this temperature. This plasmonic source sharing arrangement with reference paths also allows the removal of instability in the plasmonic source operation as a potential cause for an error in detecting a molecular recognition event. It is understood that the pattern depicted in FIG. 18A can be replicated in a 2D array and wiring can be provided to the plasmonic sources and photodetectors in the form of top and bottom electrodes.

Figure 19:
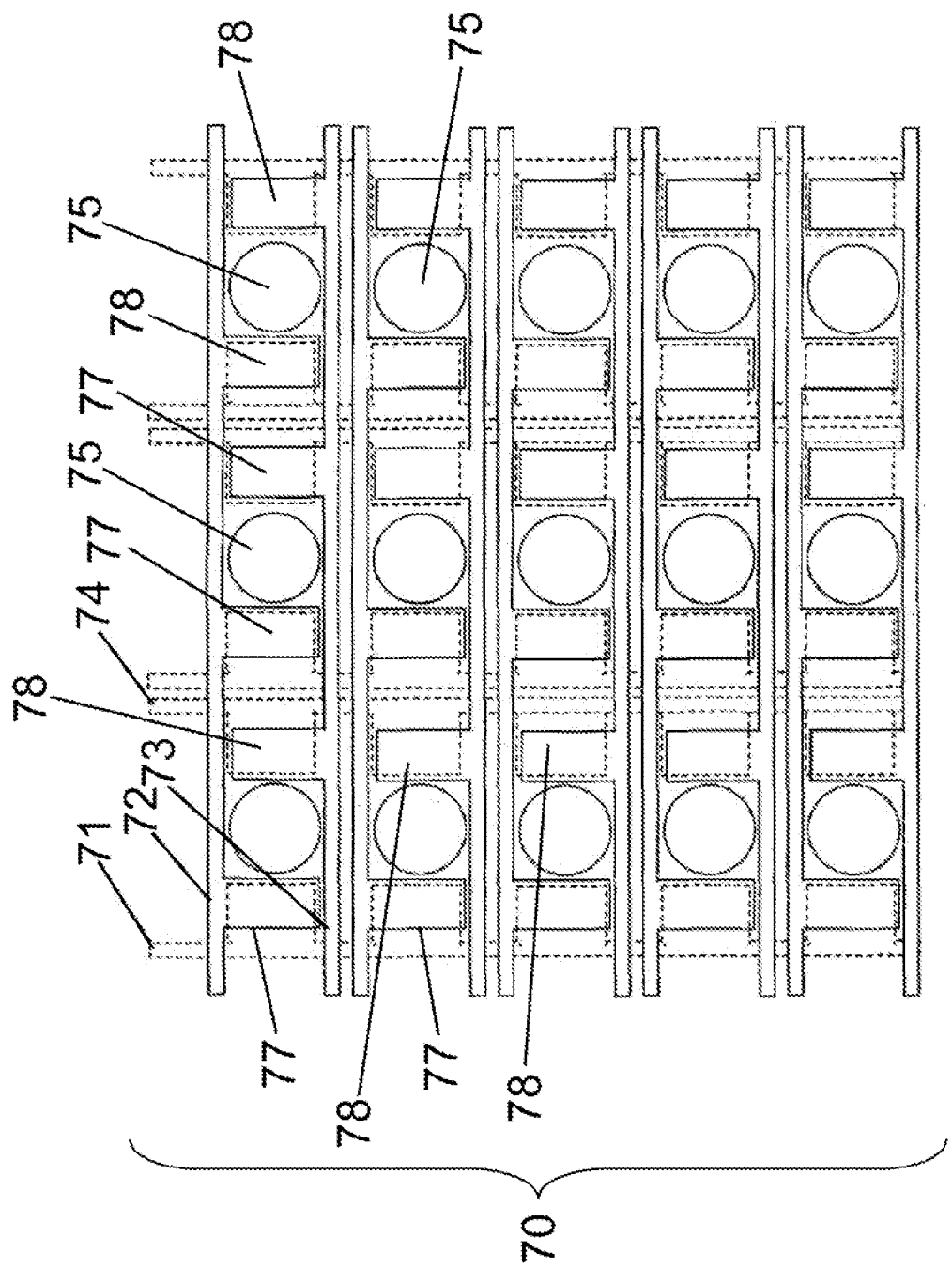
FIG. 19 illustrates a layout of a plurality of measurement regions with associated structure for determining a molecular recognition event at each measurement region.
Figure 20E:
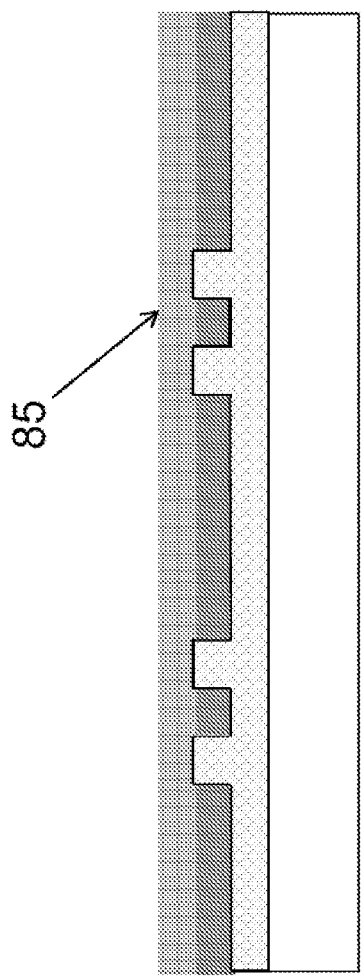
Figure 20F:
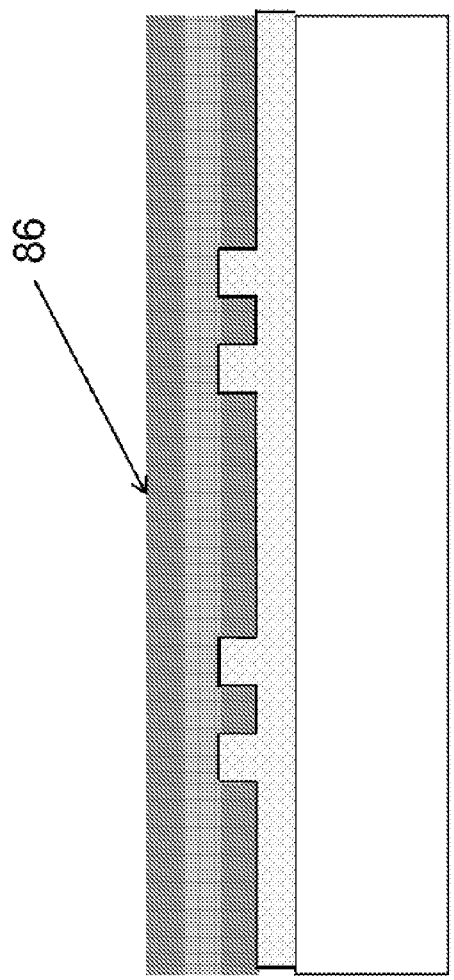
Figure 20I:
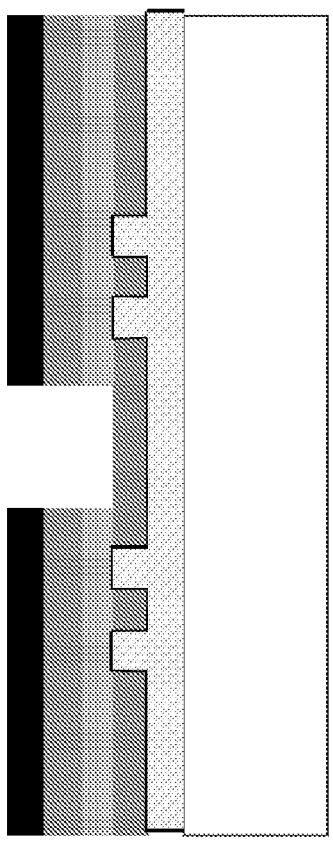
Figure 20J:
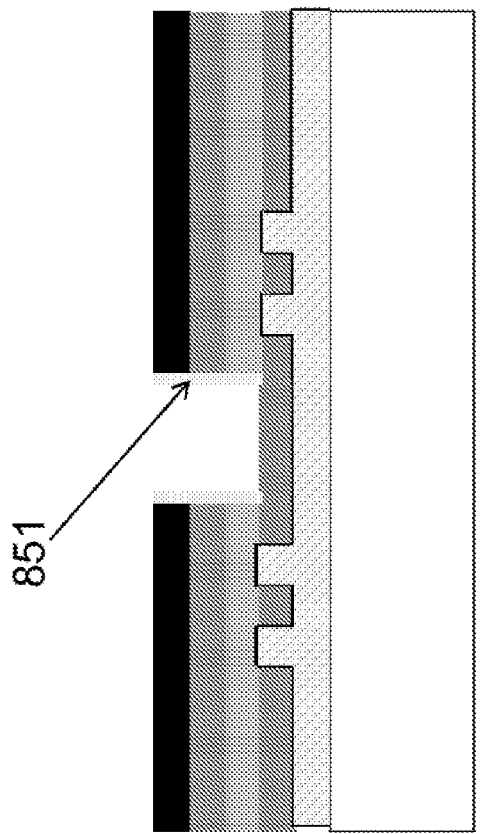

FIG. 19 illustrates a layout of another embodiment of a biochip. It consists of a plurality of measurement regions 75 and a plasmonic source 77/detector 78 pair associated with each measurement region. The biochip is arranged in rows and columns. Each row shares a common top electrode 72 of the plasmonic source 77 and a common top electrode 73 of the photodetector 78. Each column shares a common bottom electrode 71 of the plasmonic source and a common bottom electrode 74 of the photodetector. By applying signal to the appropriate row and column, one plasmonic source/photodetector pair can be activated at a time.

FIGS. 20a-k illustrate an embodiment of a method of manufacturing a biochip in accordance with subject matter described herein. The biochip shown in this embodiment includes, at each measurement region, a plasmonic source, an incident plasmonic mode excitation filtering region, an interaction region for determining a molecular recognition event in a biological substance by way of detecting an absorbing or fluorescent molecule, or in a marker-free biological substance by way of detecting a refractive index change, a secondary plasmonic mode excitation filtering region, and a thin-film detector.

A glass substrate 81 with an optical quality finish is first chemically treated to remove any particles or residues from its surface. (FIG. 20a) A patterned layer of silica is formed, for example, by forming a sol-gel and imprinting with a stamp to produce patterned layer 82 comprising structures that will form the columns of bottom electrodes for the plasmonic sources and photodetectors, incident plasmonic mode excitation filtering regions, interaction regions, and secondary plasmonic mode excitation filtering regions. (FIG. 20b) These regions are arranged in columns as illustrated in FIG. 19. A bottom electrode 83 such as a gold and silver metal bi-layer is formed by known techniques such as physical vapor deposition of gold and silver onto the patterned layer of silica. (FIG. 20c) The metal bi-layer is planarized using a known technique, such as chemical mechanical polishing (CMP). (FIG. 20d) A semiconductor small molecule organic p-n bi-layer 85 e.g., 75 nm of N,N'-diphenyl-N,N'-bis(3-methyl phenyl)-(1,1'-biphenyl)-4,4'-diamine (TPD) and 75 nm of tris(8-hydroxyquinolinato) aluminum (Alq3) is then evaporated on the planarized surface. (FIG. 20e) The formed semiconductor bi-layer will subsequently be used to form both the plasmonic sources and the thin film photodetectors. A top electrode 86 such as a silver and gold metal bi-layer is then deposited on top of the semiconductor bi-layer. (FIG. 20f) Next a layer of chromium 852 is deposited, followed by a photoresist etch mask 87 patterned to form the rows of the top electrodes for the plasmonic sources 88 and photodetectors 89, and the interaction regions 850. (FIG. 20g) These regions are arranged in rows as illustrated in FIG. 19. A chemical etch process is used to transfer the pattern into the chromium hard mask layer. (FIG. 20h) A directional plasma etch process removes material to expose the gold bottom electrode surface to define the interaction regions. (FIG. 20i) Encapsulation dielectric layers 851 are then applied using a conformal deposition process followed by directional etching or using a directional physical deposition process with the biochip mounted at an angle and rotated to create a shadow mask effect. (FIG. 20j) To complete the biochip wafer processing molecular recognition agents (probes) 853 are then formed on top of the interaction regions by one of the available techniques such as robotic spotting, inkjet printing or photolithography to form one or more measurement regions. (FIG. 20k) The biochip wafer can then be diced into individual chips which are then wire bonded into packages for individual addressing of top and bottom electrodes of the plasmonic source/photodetector pairs.

FIGS. 21a and 21b illustrate an embodiment of a third aspect of the biochip subject matter described herein comprising a method of testing a biological substance. The biological substance is disposed over a plurality of measurement regions whereby each measurement region can be interrogated and monitored individually at any point during the hybridization process independently of the other measurement regions.

FIG. 21a shows monitoring of the measurement region 95 (first in the second row) by activating the plasmonic source through signal applied between electrodes 92 and 93 and receiving signal from the photodetector electrodes 91 and 94 which contains information about the status of molecular recognition at site 95. FIG. 21b shows monitoring of another measurement region 950 (second in third row) by activating plasmonic source electrodes 97 and 98 and receiving feedback from photodetector electrodes 96 and 99. In addition to the electrodes shown in FIGS. 21a and 21b there could be additional electrodes associated with each measurement region for controlling molecular recognition conditions such as heaters to control temperature. The heaters could be made of chromium and located underneath the measurement regions, enclosed in a dielectric layer such as silicon dioxide. It is understood that in the layout shown in FIGS. 21a and 21b, a number of alternative means to determine a molecular recognition event at each measurement region could be used as described in this specification earlier.

Embodiments of plasmonic sensing devices described above can be implemented in applications wherein the plasmonic sensing device serves as a device for determining properties of light incident on the device in the absence of a test material in contact with the device. In such embodiments, the material under test is not necessarily in contact with the device in the detection region. For example, the material under test can be positioned above, below, or adjacent to, but not in contact with, the surface of the device. In such embodiments, interrogating light is applied to the material under test and the power received by the image sensor of the integrated plasmonic device varies with the illumination conditions as well as the composition of the material under test. The illumination conditions that vary include those described above, such as the angle of incidence, polarization state, wavelength, and illumination intensity. The light received by the plasmonic sensing device includes light after it interacts with the material under test. Light incident on the material under test can be absorbed by the material, transmitted by the material, reflected by the material, excite a luminescent response from the material or other substance associated with the material under test. The light received by the plasmonic device excites plasmonic excitation modes as described above which are transmitted through the plasmonic backplane to the image sensor which produces a detectable image sensor signal based on the power received.

It will be appreciated by a person skilled in the art that numerous variations and/or modifications may be made to the subject matter described herein as shown in the specific embodiments without departing from the spirit or scope of the invention as broadly described. The present embodiments are therefore to be considered in all respects illustrative and not restrictive.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, including but not limited to U.S. patent application Ser. No. 13/440,808 filed Apr. 5, 2012, which claims the benefit of U.S. Provisional Application No. 61/472,188 filed Apr. 5, 2011, and U.S. Provisional Application No. 61/472,154 filed Apr. 5, 2011, are incorporated herein by reference, in their entirety. Aspects of the embodiments can be modified, if necessary to employ concepts of the various patents, applications and publications to provide yet further embodiments.

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A monolithic sensor comprising:
   an image sensor having a plurality of photodetectors;
   a dielectric material coated over the image sensor and including a plurality of stamp-formed dielectric material features;
   a plasmonic backplane comprising a metal coating the stamped dielectric material, the plasmonic backplane including a plurality of measurement regions, with at least some of the measurement regions having plasmonic scattering features formed from the metal coated stamped dielectric material; and
   plasmon vias connecting the plasmonic scattering features to at least some of the plurality of photodetectors of the image sensor.

2. The monolithic sensor of claim 1, further comprising a fluid chamber over the plasmonic backplane.

3. The monolithic sensor of claim 1, wherein more than one of the plurality of photodetectors is connected to one of the plurality of measurement regions by one or more plasmon vias.

4. The monolithic sensor of claim 1, wherein more than one of the plurality of measurement regions is connected to one of the plurality of photodetectors by one or more plasmon via.

5. The monolithic sensor of claim 1, wherein at least some of the plurality of measurement regions is laterally offset from and connected to one or more photodetectors by one or more plasmon vias.

6. The monolithic sensor of claim 1, wherein tethered molecules for molecular recognition of biological or chemical substances are attached to at least some of the plurality of measurement regions.

* * * * *